(12) United States Patent
Lorenz et al.

(10) Patent No.: US 7,317,938 B2
(45) Date of Patent: Jan. 8, 2008

(54) METHOD OF ADAPTING IN-VITRO MODELS TO AID IN NONINVASIVE GLUCOSE DETERMINATION

(75) Inventors: Alexander D. Lorenz, Chandler, AZ (US); Timothy L. Ruchti, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 274 days.

(21) Appl. No.: 10/978,116

(22) Filed: Oct. 29, 2004

(65) Prior Publication Data
US 2005/0119541 A1    Jun. 2, 2005

Related U.S. Application Data

(63) Continuation-in-part of application No. 10/971,447, filed on Oct. 21, 2004, and a continuation-in-part of application No. 10/820,322, filed on Apr. 7, 2004, which is a continuation-in-part of application No. 09/877,529, filed on Jun. 8, 2001, now abandoned, which is a continuation-in-part of application No. 09/415,389, filed on Oct. 8, 1999, now Pat. No. 6,411,373, which is a continuation-in-part of application No. 10/472,856, filed as application No. PCT/US03/07065 on Mar. 7, 2003, now Pat. No. 7,133,710.

(60) Provisional application No. 60/532,602, filed on Dec. 23, 2003, provisional application No. 60/518,136, filed on Nov. 6, 2003, provisional application No. 60/362,885, filed on Mar. 8, 2002.

(51) Int. Cl.
*A61B 5/00* (2006.01)

(52) U.S. Cl. .................. 600/316; 600/310

(58) Field of Classification Search ............... 600/310, 600/316, 322
See application file for complete search history.

(56) References Cited

U.S. PATENT DOCUMENTS

| | | | |
|---|---|---|---|
| 5,007,423 A | 4/1991 | Branstetter et al. | |
| 5,068,536 A | 11/1991 | Rosenthal | |
| 5,077,476 A | 12/1991 | Rosenthal | |
| 5,507,288 A | 4/1996 | Bocker et al. | |
| 5,596,987 A | 1/1997 | Chance | |
| 5,632,273 A | 5/1997 | Suzuki | |
| 5,825,488 A | 10/1998 | Kohl et al. | |
| 5,879,373 A | 3/1999 | Roper et al. | |
| 6,040,578 A | 3/2000 | Malin et al. | |
| 6,421,548 B1 | 7/2002 | Berman et al. | |
| 6,441,388 B1 * | 8/2002 | Thomas et al. | ............. 250/573 |

\* cited by examiner

*Primary Examiner*—Eric F Winakur
(74) *Attorney, Agent, or Firm*—Michael A. Glenn; Glenn Patent Group

(57) ABSTRACT

The invention relates to a noninvasive analyzer and a method of using information determined at least in part from in-vitro spectra of tissue phantoms or analyte solutions to aid in the development of a noninvasive glucose concentration analyzer and/or in the analysis of noninvasive spectra resulting in glucose concentration estimations in the body. The preferred apparatus is a spectrometer that includes a base module and a sample module that is semi-continuously in contact with a human subject and that collects spectral measurements which are used to determine a biological parameter in the sampled tissue, such as glucose concentration. Collection of in-vitro samples is, optionally, performed on a separate instrument from the production model allowing the measurement technology to be developed on a research grade instrument and used or transferred to a target product platform or production analyzer for noninvasive glucose concentration estimation.

66 Claims, 13 Drawing Sheets

METHOD OF ADAPTING IN-VITRO MODELS TO AID IN NONINVASIVE GLUCOSE DETERMINATION

CROSS REFERENCE TO RELATED APPLICATIONS

This application claims benefit of U.S. Provisional Patent Application Ser. No. 60/518,136, filed Nov. 6, 2003, and is a continuation-in-part of:

U.S. patent application Ser. No. 10/971,447, filed Oct. 21, 2004, which claims benefit of U.S. Provisional Patent Application Ser. No. 60/532,602, filed Dec. 23, 2003;

U.S. patent application Ser. No. 10/820,322, filed Apr. 7, 2004, which is a Continuation-in-part of U.S. patent application Ser. No. 09/877,529, filed Jun. 8, 2001, now abandoned, which is a Continuation-in-part of U.S. patent application Ser. No. 09/415,389, filed Oct. 8, 1999, now U.S. Pat. No. 6,411,373 (Jun. 25, 2002); and U.S. patent application Ser. No. 10/472,856, filed Sep. 18, 2003, now U.S. Pat. No. 7,133,710 (Oct. 18, 2006), which claims priority from PCT Application No. PCT/US03/07065, filed Mar. 7, 2003, which claims benefit of U.S. Provisional Patent Application Ser. No. 60/362,885, filed Mar. 8, 2002, each of which is incorporated herein in its entirety by this reference thereto.

BACKGROUND OF THE INVENTION

1. Field of the Invention

The invention relates generally to a method and apparatus of noninvasive glucose concentration estimation. More particularly, the invention relates to a method of adapting in-vitro models to aid in noninvasive glucose determination.

2. Description of Related Art

Spectroscopy-based noninvasive analyzers deliver external energy in the form of light to a specific sample site, region, or volume of the human body, wherein the photons interact with a tissue sample, thus probing chemical and physical features. A portion of the incident photons are specularly reflected, diffusely reflected, scattered, or transmitted out of the body and are subsequently detected. Based upon knowledge of the incident photons and the detected photons, the chemical and/or structural basis of the sampled site is deduced. A distinct advantage of a noninvasive analyzer is the ability to analyze chemical and structural constituents in the body in a pain-free manner while limiting both consumables and possible generation of biohazards. Additionally, noninvasive analyzers allow multiple analytes or structural features to be determined at one time. Common examples of noninvasive analyzers are those using magnetic resonance imaging (MRI) or x-rays, pulse oximeters, and noninvasive glucose concentration analyzers. With the exception of x-rays, these determinations are performed using relatively harmless wavelengths of radiation. Examples described herein focus on noninvasive glucose concentration estimation, but the principles apply to other noninvasive measurements and/or determination of additional blood or tissue analytes.

Diabetes

Diabetes is a chronic disease that results in abnormal production and use of insulin, a hormone that facilitates glucose uptake into cells. While a precise cause of diabetes is unknown, genetic factors, environmental factors, and obesity play roles. Diabetics have an increased health risk in three broad categories: cardiovascular heart disease, retinopathy, and neuropathy. Diabetics often have one or more of the following complications: heart disease and stroke, high blood pressure, kidney disease, neuropathy (nerve disease and amputations), retinopathy, diabetic ketoacidosis, skin conditions, gum disease, impotence, and fetal complications. Diabetes is a leading cause of death and disability worldwide. Moreover, diabetes is merely one among a group of disorders of glucose metabolism that also includes impaired glucose tolerance and hyperinsulinemia, which is also known as hypoglycemia.

Diabetes Prevalence and Trends

The prevalence of individuals with diabetes is increasing with time. The World Health Organization (WHO) estimates that diabetes currently afflicts 154 million people worldwide. There are 54 million people with diabetes living in developed countries. The WHO estimates that the number of people with diabetes will grow to 300 million by the year 2025. In the United States, 15.7 million people or 5.9 percent of the population are estimated to have diabetes. Within the United States, the prevalence of adults diagnosed with diabetes increased by 6% in 1999 and rose by 33% between 1990 and 1998. This corresponds to approximately eight hundred thousand new cases every year in America. The estimated total cost to the United States economy alone exceeds $90 billion per year. [*Diabetes Statistics*, National Institutes of Health, Publication No. 98-3926, Bethesda, Md. (November 1997)].

Long-term clinical studies demonstrate that the onset of diabetes related complications is significantly reduced through proper control of blood glucose concentrations. See, for example, The Diabetes Control and Complications Trial Research Group, *The effect of intensive treatment of diabetes on the development and progression of long-term complications in insulin-dependent diabetes mellitus*, N. Eng. J. of Med., 329:977-86 (1993); U.K. Prospective Diabetes Study (UKPDS) Group, *Intensive blood-glucose control with sulphonylureas or insulin compared with conventional treatment and risk of complications in patients with type 2 diabetes*, Lancet, 352:837-853 (1998); and Y. Ohkubo, H. Kishikawa, E. Araki, T. Miyata, S. Isami, S. Motoyoshi, Y. Kojima, N. Furuyoshi, M. Shichizi, *Intensive insulin therapy prevents the progression of diabetic microvascular complications in Japanese patients with non-insulin-dependent diabetes mellitus: a randomized prospective 6-year study*, Diabetes Res. Clin. Pract., 28:13-117 (1995).

A vital element of diabetes management is the self-monitoring of blood glucose concentration by diabetics in the home environment. However, current monitoring techniques discourage regular use due to the inconvenient and painful nature of drawing blood or interstitial fluid through the skin prior to analysis, (The Diabetes Control and Complication Trial Research Group, supra). As a result, noninvasive measurement of glucose concentration is identified as a beneficial development for the management of diabetes. Implantable glucose concentration analyzers coupled to an insulin delivery system providing an artificial pancreas are also being pursued.

Noninvasive Glucose Concentration Determination

There exist a number of noninvasive approaches for glucose concentration determination. These approaches vary widely, but have at least two common steps. First, an apparatus is used to acquire a reading from the body without obtaining a biological sample. Second, an algorithm converts this reading into a glucose concentration estimation.

One species of noninvasive glucose concentration analyzers includes those based upon the collection and analysis of spectra. Typically, a noninvasive apparatus uses some form of spectroscopy to acquire the signal or spectrum from the body. Spectroscopic techniques include but are not limited to Raman and fluorescence, as well as techniques using light from ultraviolet through the infrared [ultraviolet (200 to 400 nm), visible (400 to 700 nm), near-infrared (700 to 2500 nm or 14,286 to 4000 $cm^{-1}$), and infrared (2500 to 14,285 nm or 4000 to 700 $cm^{-1}$)]. A particular range for noninvasive glucose determination in diffuse reflectance mode is about 1100 to 2500 nm or ranges therein. See, for example, K. Hazen *Glucose determination in biological matrices using near-infrared spectroscopy*, doctoral dissertation, University of Iowa, (1995). It is important to note, that these techniques are distinct from the traditional invasive and alternative invasive techniques listed above in that the sample analyzed is a portion of the human body in-situ, not a biological sample acquired from the human body.

Typically, three modes are used to collect noninvasive scans: transmittance, transflectance, and/or diffuse reflectance. For example the light, spectrum, or signal collected is light transmitted through a region of the body, diffusely transmitted, diffusely reflected, or transflected. Transflected refers to collection of the signal not at the incident point or area (diffuse reflectance), and not at the opposite side of the sample (transmittance), but rather at some point or region of the body between the transmitted and diffuse reflectance collection area. For example, transflected light enters the fingertip or forearm in one region and exits in another region. When using the near-infrared to sample skin tissue, the transflected radiation typically radially disperses 0.2 to 5 mm or more away from the incident photons depending on the wavelength used. For example, light that is strongly absorbed by the body, such as light near the water absorbance maxima at 1450 or 1950 nm, is collected after a small radial divergence in order to be detected and light that is less absorbed, such as light near water absorbance minima at 1300, 1600, or 2250 nm is, optionally, collected at greater radial or transflected distances from the incident photons.

Noninvasive techniques are used to analyze tissue and/or blood. Regions or volumes of the body subjected to noninvasive measurements include: a hand, finger, fingertip, palmar region, base of thumb, forearm, volar aspect of the forearm, dorsal aspect of the forearm, upper arm, head, earlobe, eye, tongue, chest, torso, abdominal region, thigh, calf, foot, plantar region, and toe. Notably, noninvasive techniques are not necessarily based upon spectroscopy. For example, a bioimpedence meter is a noninvasive device. In this document, any device that reads or determines a glucose concentration from the body without penetrating the skin and collecting a biological sample is referred to as a noninvasive glucose concentration analyzer. Some noninvasive analyzers use invasive methods for purposes of calibration or bias correction of estimated glucose concentration values.

Calibration

Optical based glucose concentration analyzers require calibration. This is true for all types of glucose concentration analyzers, such as traditional invasive, alternative invasive, noninvasive, and implantable analyzers. A fundamental feature of noninvasive glucose concentration analyzers is that they are secondary in nature, that is, they do not measure blood glucose concentrations directly. Therefore, a primary method is required to calibrate these devices to measure blood glucose concentrations properly. Many methods of calibration exist.

One noninvasive technology, near-infrared spectroscopy, requires that a mathematical relationship between an in-vivo near-infrared spectrum and the actual blood glucose concentration is developed. This relationship is achieved through the collection of in-vivo near-infrared measurements with corresponding blood glucose concentrations that are obtained directly through the use of measurement tools, such as a traditional invasive or alternative invasive reference device.

For spectrophotometric based analyzers, there are several univariate and multivariate methods that are used to develop the mathematical relationship between the measured signal and the actual blood glucose concentration. However, the basic equation being solved is known as the Beer-Lambert Law. This approximation states that the strength of an absorbance/reflectance measurement is proportional to the concentration of the analyte which is being measured, as in equation 1, $$A = \epsilon b C \quad (1)$$

where A is the absorbance/reflectance measurement at a given wavelength of light, $\epsilon$ is the molar absorptivity associated with the molecule of interest at the same given wavelength, b is the distance that the light travels, and C is the concentration of the molecule of interest (glucose).

Chemometric calibration techniques extract a glucose or glucose-related signal from acquired spectra through various methods of signal processing and calibration including one or more mathematical models. The models are developed through the process of calibration on the basis of an exemplary set of spectral measurements known as the calibration set and an associated set of reference blood glucose concentrations based upon an analysis of capillary blood or venous blood. Common multivariate approaches, requiring an exemplary reference glucose concentration for each sample spectrum in a calibration, include partial least squares (PLS) and principal component regression (PCR). Many additional forms of calibration are known to those skilled in the art.

There are a number of reports of noninvasive glucose technologies. Some of these relate to general instrumentation configurations required for noninvasive glucose concentration determination while others refer to sampling technologies. Those related to the present invention are briefly reviewed here:

General Instrumentation

Pulse oximeters operate on wavelengths about 660 and 805 nm, which correlate oxy-hemoglobin and deoxy-hemoglobin absorbance bands. Siemens, A G, Verfahren und Gerät zur kolorimetrischen Untersuchung von Substanzen auf signifikante bestandteile (Method and device for a calorimetric examination of substances for significant components), DE 2,255,300, filed Nov. 11, 1972 describes a pulse oximeter meter operating in a spectral region of 600 to 900 nm, which is at shorter wavelengths than the noninvasive glucose concentration meters of this invention that operate from about 1100 to 2500 nm or ranges therein.

K. Schlager, Non-invasive near infrared measurement of blood analyte concentrations, U.S. Pat. No. 4,882,492 (Nov. 21, 1989) describes a dual beam noninvasive glucose analyzer. This patent is commonly owned with the current application.

R. Barnes, J. Brasch, D. Purdy, W. Lougheed, Non-invasive determination of analyte concentration in body of mammals, U.S. Pat. No. 5,379,764 (Jan. 10, 1995) describe a noninvasive glucose concentration determination analyzer that uses data pretreatment in conjunction with a multivariate analysis to determine blood glucose concentrations.

P. Rolfe, Investigating substances in a patient's bloodstream, UK Patent Application Ser. No. 2,033,575 (Aug. 24, 1979) describes an apparatus for directing light into the body, detecting attenuated backscattered light, and using the collected signal to determine glucose concentrations in or near the bloodstream.

C. Dahne, D. Gross, Spectrophotometric method and apparatus for the non-invasive, U.S. Pat. No. 4,655,225 (Apr. 7, 1987) describe a method and apparatus for directing light into a patient's body, collecting transmitted or backscattered light, and determining glucose concentrations from selected near-infrared (near-IR) wavelength bands. Wavelengths include 1560 to 1590, 1750 to 1780, 2085 to 2115, and 2255 to 2285 nm, with at least one additional reference signal from 1000 to 2700 nm.

M. Robinson, K. Ward, R. Eaton, D. Haaland, Method and apparatus for determining the similarity of a biological analyte from a model constructed from known biological fluids, U.S. Pat. No. 4,975,581 (Dec. 4, 1990) describe a method and apparatus for measuring a concentration of a biological analyte, such as glucose using infrared spectroscopy in conjunction with a multivariate model. The multivariate model is constructed from a plurality of known biological fluid samples.

J. Hall, T. Cadell, Method and device for measuring concentration levels of blood constituents non-invasively, U.S. Pat. No. 5,361,758 (Nov. 8, 1994) describe a noninvasive device and method for determining analyte concentrations within a living subject using polychromatic light, a wavelength separation device, and an array detector. The apparatus uses a receptor shaped to accept a fingertip with means for blocking extraneous light.

S. Malin, G Khalil, Method and apparatus for multispectral analysis of organic blood analytes in noninvasive infrared spectroscopy, U.S. Pat. No. 6,040,578 (Mar. 21, 2000) describe a method and apparatus for determination of an organic blood analyte using multi-spectral analysis in the near-infrared. A plurality of distinct nonoverlapping spectral regions of wavelengths is incident upon a sample surface, diffusely reflected radiation is collected, and the analyte concentration is determined via chemometric techniques. This patent is commonly owned with the current application.

J. Garside, S. Monfre, B. Elliott, T. Ruchti, G. Kees, Fiber optic illumination and detection patterns, shapes, and locations for use in spectroscopic analysis, U.S. Pat. No. 6,411,373 (Jun. 25, 2002) describe the use of fiber optics for use as excitation and/or collection optics with various spatial distributions. This patent is commonly owned with the current application.

Specular Reflectance

R. Messerschmidt, D. Sting Blocker device for eliminating specular reflectance from a diffuse reflectance spectrum, U.S. Pat. No. 4,661,706 (Apr. 28, 1987) describe a reduction of specular reflectance by a mechanical device. A blade-like device skims the specular light before it impinges on the detector. This system leaves alignment concerns and improvement in efficiency of collecting diffusely reflected light is needed.

R. Messerschmidt, M. Robinson Diffuse reflectance monitoring apparatus, U.S. Pat. No. 5,636,633 (Jun. 10, 1997) describe a specular control device for diffuse reflectance spectroscopy using a group of reflecting and open sections.

R. Messerschmidt, M. Robinson Diffuse reflectance monitoring apparatus, U.S. Pat. No. 5,935,062 (Aug. 10, 1999) and R. Messerschmidt, M. Robinson Diffuse reflectance monitoring apparatus, U.S. Pat. No. 6,230,034 (May 8, 2001) describe a diffuse reflectance control device that discriminates between diffusely reflected light that is reflected from selected depths. This control device additionally acts as a blocker to prevent specularly reflected light from reaching the detector.

Malin, supra, describes the use of specularly-reflected light in regions of high water absorbance, such as 1450 and 1900 nm, to mark the presence of outlier spectra wherein the specularly reflected light is not sufficiently reduced. This patent is commonly owned with the current application.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe a mechanical device for applying sufficient and reproducible contact of the apparatus to the sample medium to minimize specular reflectance. Further, the apparatus allows for reproducible applied pressure to the sample site and reproducible temperature at the sample site. This patent is commonly owned with the current application.

Sample Preparation

B. Wenzel, S. Monfre, T. Ruchti, K. Meissner, F. Grochocki, T. Blank, J. Rennert, A method for quantification of stratum corneum hydration using diffuse reflectance spectroscopy, U.S. Pat. No. 6,442,408 (Aug. 27, 2002) describe a method and apparatus for determination of tissue variability, such as water content of the epidermal ridge and penetration depth of incident light. This patent is commonly owned with the current application.

Temperature

K. Hazen, *Glucose determination in biological matrices using near-Infrared spectroscopy,* doctoral dissertation, University of Iowa (1995) describes the adverse effect of temperature on near-infrared based glucose concentration estimations. Physiological constituents have near-infrared absorbance spectra that are sensitive, in terms of magnitude and location, to localized temperature and the sensitivity impacts noninvasive glucose concentration estimation.

Coupling Fluid

A number of sources describe coupling fluids as a consideration in an optical sampling method or apparatus.

Index of refraction matching between the sampling apparatus and sampled medium is well known. Glycerol is commonly used to match refractive indices of optics and skin.

R. Messerschmidt, Method for non-invasive blood analyte measurement with improved optical interface, U.S. Pat. No. 5,655,530 (Aug. 12, 1997), and R. Messerschmidt Method for non-invasive blood analyte measurement with improved optical interface, U.S. Pat. No. 5,823,951 describe an index-matching medium for use between a sensor probe and the skin surface. The index-matching medium is a composition containing perfluorocarbons and chlorofluorocarbons.

M. Robinson, R. Messerschmidt, Method for non-invasive blood analyte measurement with improved optical interface, U.S. Pat. No. 6,152,876 (Nov. 28, 2000) and M. Rohrscheib, C. Gardner, M. Robinson, Method and apparatus for non-invasive blood analyte measurement with fluid compartment equilibration, U.S. Pat. No. 6,240,306 (May 29, 2001) describe an index-matching medium to improve the interface between the sensor probe and skin surface during spectroscopic analysis. The index-matching medium is preferably a composition containing chlorofluorocarbons with optional perfluorocarbons.

T. Blank, G. Acosta, M. Mattu, S. Monfre, Fiber optic probe guide placement guide, U.S. Pat. No. 6,415,167 (Jul. 2, 2002) describe a coupling fluid of one or more perfluoro compounds where a quantity of the coupling fluid is placed at an interface of the optical probe and measurement site. Advantageously, perfluoro compounds lack the toxicity associated with chlorofluorocarbons. This patent is commonly owned with the current application.

Positioning

T. Blank, supra, describes the use of a guide in conjunction with a noninvasive glucose concentration analyzer in order to increase precision of the location of the sampled tissue site resulting in increased accuracy and precision in noninvasive glucose concentration estimations. This patent is commonly owned with the current application.

J. Griffith, P. Cooper, T. Barker, Method and apparatus for non-invasive blood glucose sensing, U.S. Pat. No. 6,088,605 (Jul. 11, 2000) describe an analyzer with a patient forearm interface in which the forearm of the patient is moved in an incremental manner along the longitudinal axis of the patient's forearm. Spectra collected at incremental distances are averaged to take into account variations in the biological components of the skin. Between measurements rollers are used to raise the arm, move the arm relative to the apparatus and lower the arm by disengaging a solenoid causing the skin lifting mechanism to lower the arm into a new contact with the sensor head. The Griffith teachings do not suggest the use of a controlled pressure between the forearm sample site and the sampling head. In addition, spectra are not collected during a period of relative motion between the sample and the analyzer.

Pressure

E. Chan, B. Sorg, D. Protsenko, M. O'Neil, M. Motamedi, A. Welch, *Effects of compression on soft tissue optical properties*, IEEE Journal of Selected Topics in Quantum Electronics, Vol. 2, no. 4, 943-950 (1996) describe the effect of pressure on absorption and reduced scattering coefficients from 400 to 1800 nm. Most specimens show an increase in the scattering coefficient with compression.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe in a first embodiment a noninvasive glucose concentration estimation apparatus for either varying the pressure applied to a sample site or maintaining a constant pressure on a sample site in a controlled and reproducible manner by moving a sample probe along the z-axis perpendicular to the sample site surface. In an additional described embodiment, the arm sample site platform is moved along the z-axis that is perpendicular to the plane defined by the sample surface by raising or lowering the sample holder platform relative to the analyzer probe tip. The U.S. Pat. No. 6,534,012 further teaches proper contact between the probe tip and the sample site to be that point at which specularly-reflected light is substantially zero at the water bands at 1950 and 2500 nm. This patent is commonly owned with the current application.

M. Makarewicz, M. Mattu, T. Blank, G. Acosta, E. Handy, W. Hay, T. Stippick, B. Richie, Method and apparatus for minimizing spectral interference due to within and between sample variations during in-situ spectral sampling of tissue, U.S. patent application Ser. No. 09/954,856 (filed Sep. 17, 2001) describe a temperature and pressure controlled sample interface. The means of pressure control is a set of supports for the sample that control the natural position of the sample probe relative to the sample. This patent is commonly owned with the current application.

Data Processing

R. Barnes, J. Brasch, Non-invasive determination of glucose concentration in body of patients, U.S. Pat. No. 5,070,874 (Dec. 10, 1991) describe a method of collecting near-infrared noninvasive spectra, preprocessing with an $n^{th}$ derivative, and determining a glucose concentration from the resulting spectrum.

Several approaches exist that employ diverse preprocessing methods to remove spectral variation related to the sample and instrumental variation including normalization, smoothing, derivatives, multiplicative signal correction, [P. Geladi, D. McDougall, H. Martens *Linearization and scatter-correction for near-infrared reflectance spectra of meat*, Applied Spectroscopy, vol. 39, 491-500 (1985)], standard normal variate transformation, [R. Barnes, M. Dhanoa, S. Lister, Applied Spectroscopy, 43, 772-777 (1989)], piecewise multiplicative scatter correction, [T. Isaksson and B. Kowalski, Applied Spectroscopy, 47, 702-709 (1993)], extended multiplicative signal correction, [H. Martens, E. Stark, *J. Pharm Biomed Anal*, 9, 625-635 (1991)], pathlength correction with chemical modeling and optimized scaling, [*GlucoWatch automatic glucose biographer and autosensors*, Cygnus Inc., Document #1992-00 (Rev. March 2001)], and finite impulse response filtering, [S. Sum, *Spectral signal correction for multivariate calibration*, Doctoral Dissertation, University of Delaware (1998); S. Sum, and S. Brown, *Standardization of fiber-optic probes for near-infrared multivariate Calibrations*, Applied Spectroscopy, Vol. 52, No. 6, 869-877 (1998); and T. Blank, S. Sum, S. Brown, S. Monfre, *Transfer of near-infrared multivariate calibrations without standards*, Analytical Chemistry, 68, 2987-2995 (1996)].

In addition, a diversity of signal, data or pre-processing techniques are commonly reported with the fundamental goal of enhancing accessibility of the net analyte signal [D. Massart, B. Vandeginste, S. Deming, Y. Michotte, L. Kaufman, *Chemometrics: a textbook*, New York, Elsevier Science Publishing Company, Inc., 215-252 (1990); A. Oppenheim, R. Schafer, *Digital Signal Processing*, Englewood Cliffs, N.J.: Prentice Hall, 1975, 195-271; M. Otto, *Chemometrics*, Weinheim: Wiley-VCH, 51-78 (1999); K. Beebe, R. Pell, M. Seasholtz, *Chemometrics A Practical Guide*, New York: John Wiley & Sons, Inc., 26-55 (1998); M. Sharaf, D. Illman and B. Kowalski, *Chemometrics*, New York: John Wiley & Sons, Inc., 86-112 (1996); and A. Savitzky, M. Golay, *Smoothing and differentiation of data by simplified least squares procedures*, Anal. Chem., vol. 36, no. 8, 1627-1639 (1964). A goal of these techniques is to attenuate the noise and instrument variation while maximizing the signal of interest.

While methods for preprocessing partially compensate for variation related to instrument and physical changes in the sample and enhance the net analyte signal in the presence of noise and interference, they are often inadequate for compensating for the sources of tissue-related variation. For example, the highly nonlinear effects related to sampling different tissue locations are not effectively compensated for through a pathlength correction because the sample is multi-layered and heterogeneous. In addition, fundamental assumptions inherent in these methods, such as the constancy of multiplicative and additive effects across the spectral range and homoscadasticity of noise are violated in the non-invasive tissue application.

Currently, no device using near-infrared spectroscopy for the noninvasive measurement of glucose has been approved for use by persons with diabetes due to technology limitations that include poor sensitivity, sampling problems, time lag, calibration bias, long-term reproducibility, stability, and instrument noise. Further, current reported versions of noninvasive glucose concentration analyzers do not consistently yield accurate estimations of glucose concentrations in long-term patient trials in the hands of a typical user or professional operator. Further limitations to commercialization include a poor form factor (large size, heavy weight, and no or poor portability) and usability. There exists, therefore, a long-felt need for a noninvasive approach to the estimation of glucose concentration that provides long-term accurate and precise glucose concentration estimations in a semi-continuous, continuous or semi-automated fashion. Development in this area is complicated by the very expensive in-vivo testing that is necessary on human subjects. Therefore, it is of great benefit to build a model, at least in part, using a set of in-vitro samples. The in-vitro samples are cheaper and are more readily controlled. This allows tight control of the experimental conditions, such as sampling, environmental conditions, pathlength, noise, and analyte and interference concentrations.

SUMMARY OF THE INVENTION

The invention relates to a noninvasive analyzer and a method of using information determined from in-vitro spectra of tissue phantoms or analyte solutions to aid in the development of a noninvasive glucose concentration analyzer and in the analysis of noninvasive spectra, resulting in glucose concentration estimations in the body. More particularly, a tissue phantom that contains key optical parameters present in the in-vivo matrix in terms of absorbance and/or scattering is used to develop a glucose analyzer and/or a calibration model that is applied to an in-vivo spectrum to estimate a subject's glucose concentration. The preferred apparatus is a spectrometer that includes a base module and a sample module that is semi-continuously in contact with a human subject and collects spectral measurements that are used to determine a biological parameter in the sampled tissue, such as glucose concentration. Models are built, at least in part, using a set of in-vitro samples. The in-vitro samples are more readily controlled than in-vivo samples allowing tighter control of experimental conditions, such as sampling, environmental conditions, pathlength, noise, and analyte and interference concentrations. In addition, collection of in-vitro samples is optionally performed on a separate instrument from the production model allowing the measurement technology to be developed on a research grade instrument and used or transferred to a target product platform for noninvasive glucose concentration estimation.

DETAILED DESCRIPTION

Figure 1:
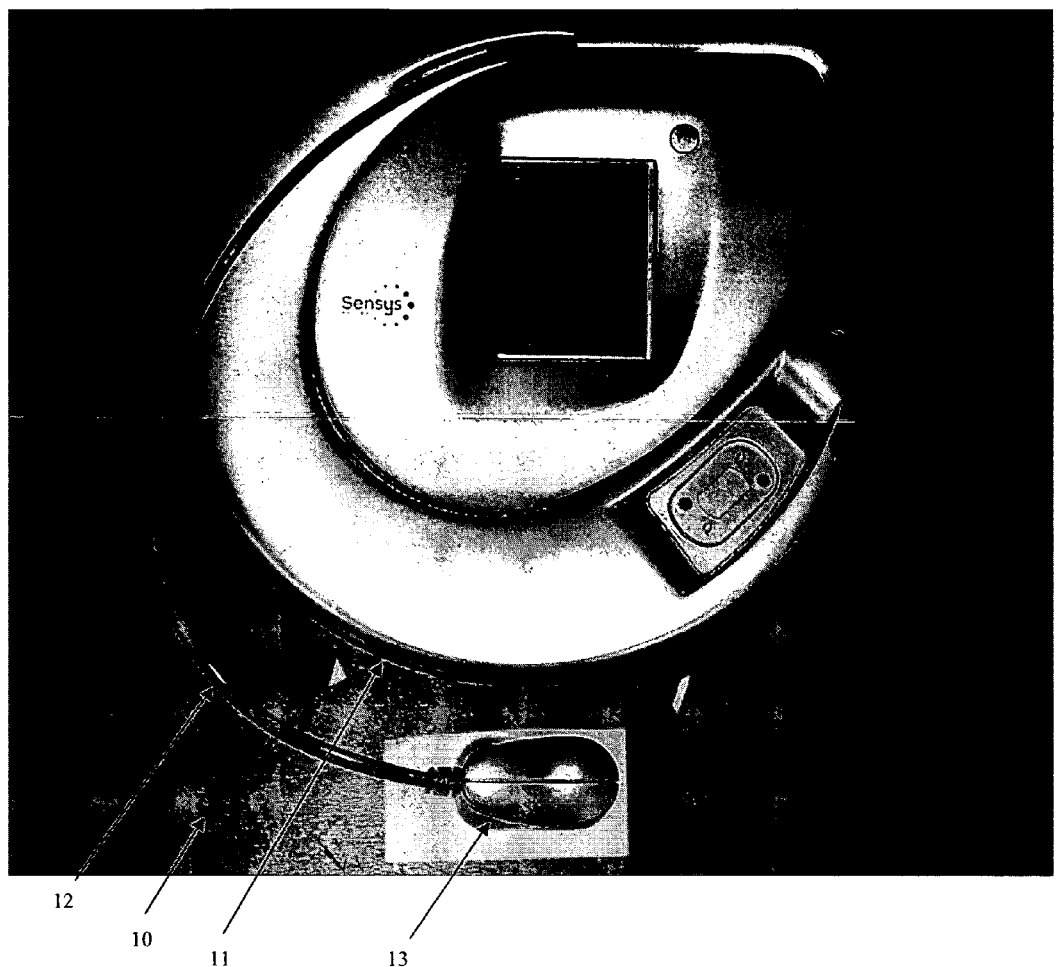
FIG. 1 is a perspective view of a glucose tracking system analyzer according to the invention.

The following detailed description should be read with reference to the drawings in which similar elements in different drawings are numbered the same. The drawings, which are not necessarily to scale, depict illustrative embodiments that are not intended to limit the scope of the invention.

The method relates to the use of spectra collected in-vitro from tissue phantoms and models generated from this in-vitro data to aid in the estimation of noninvasive glucose concentrations from noninvasive spectra. The apparatus includes a base module and a sample module coupled via optical and/or electrical communications.

The development of a near-infrared noninvasive glucose concentration estimation calibration model is usually very expensive due to the extensive in-vivo testing that is necessary on human subjects. Use of less costly in-vitro data is beneficial due to the option of tight control of the experimental conditions, such as sampling, environmental conditions, pathlength, noise, and analyte and interference concentrations. Further, the in-vitro data is optionally collected on a research grade or remote analyzer and the data or model is later transferred to a target product platform for noninvasive glucose concentration estimation.

The design and development of instruments and devices for measuring a target variable or analyte in a sample through indirect means, such as near-infrared analysis of glucose concentration in the body, requires the development of a calibration model that transforms the instrument response to an estimate of the analyte property. For example, noninvasive estimation of blood and/or tissue glucose concentration using near-infrared spectroscopy requires a model to convert the optical signal to a glucose concentration. The instrument response is the intensity or absorbance of the tissue sample measured by an analyzer or spectrometer. The calibration model estimates the glucose concentration in the tissue sample using the measured spectrum. Typically, the process of calibrating an instrument for a particular application begins with the collection of a set of samples with the instrument and a reference device. The resulting calibration data set, includes a data set of paired responses. The paired responses include an instrument response x and a reference analyte value or concentration y. Typically the instrument response is a vector and the reference analyte concentration is a single value or a set of values used as a point.

The process of calibration is the development of a mathematical model on the basis of empirical data that estimates a target variable y from an instrument response x. In the example of noninvasive blood glucose concentration estimation through the use of near-infrared spectroscopy, the instrument response is a set of responses corresponding to a set of wavelengths or is a set of responses over a continuous region and the target variable is the subject's blood glucose concentration. The process of calibration involves the determination of a model g( ), where the subject's blood glucose concentration is estimated given a response spectrum, such as an intensity or absorbance spectrum, according to equation 2

$$\hat{y} = g(x) \quad (2)$$

where $\hat{y}$ is the estimated glucose concentration and x is the instrument response.

The set of data used to determine a model g( ) is denoted as the calibration set and includes N data points of measurement spectra x and associated reference glucose concentrations y where N is an integer greater than or equal to 1. The instrument response contains the signal of interest related to the concentration of the analyte, interference, and noise. The interference reduces the accessible portion of the signal by varying simultaneously and/or in an overlapping manner with the signal. The portion of the signal that is discriminated from the interference due to its uniqueness is the net analyte signal.

The development of a near-infrared noninvasive glucose concentration estimation calibration model is usually very expensive due to the extensive in-vivo testing that is necessary on human subjects. Therefore, it is of great benefit to build a model, at least in part, using a set of in-vitro samples. For example, deriving a model from data that is 100, 80, 60, 40, or 20 percent in-vitro is beneficial in that less in-vivo data is required. The in-vitro samples are less costly and are more readily controlled. This allows tight control of the experimental conditions, such as sampling, environmental conditions, pathlength, noise, and analyte and interference concentrations. In addition, collection of in-vitro samples is optionally performed on a separated instrument from the production model. This allows the measurement technology to be developed on a research grade instrument. These approaches allow at least part of the model to be developed in a laboratory and later transferred and used on a target product platform for noninvasive glucose concentration estimation.

The invention presented herein teaches a process for calibration development, instrument design, calibration transfer, and/or component or parameter selection that significantly reduces the necessity of experimentation. In addition, methods for designing signal processing systems and for automating calibration development are presented. The methods exploit the net analyte signal present in the instrument response of the originating technology development and enable the transfer of the research with or without limited further experimentation.

Calibration Development

A tissue simulating phantom is developed that has key optical properties of an in-vivo matrix, described in detail below. The tissue phantom includes at least one of:
  key body/tissue matrix constituents are present in the tissue phantom;
  sample constituents that approximate skin constituents;
  scattering constituents that approximate a tissue sample; and
  sample constituents present over a range of physiological concentrations.

The measured spectra, associated analyte concentrations, and experimental design preferably include:
  a signal comparable to that of a noninvasive in-vivo spectrum of skin tissue in terms of absorbance magnitude, location, and/or resolution;
  scattering characteristics approximating skin;
  absorbance characteristics approximating skin;
  a noise structure that approximates that of a noninvasive spectrum;
  a set of glucose concentrations that are not correlated with time;
  a set of glucose concentrations that are not correlated with additional sample constituents, such as protein, fat, or water;
  a set of glucose concentrations that are not correlated with additional sample constituent concentrations;
  thermal noise;
  adequate resolution of sample constituents; and/or
  a controlled and/or known set of environmental conditions.

This allows a net analyte signal (NAS), of at least one sample constituent, to be determined.

A designed in-vitro experiment is performed to collect a calibration set that is infeasible, difficult, or expensive in the in-vivo matrix. An in-vivo calibration model W is determined on the basis of the calibration set and the net analyte signal is calculated, as in equation 3, $$NAS = \frac{W}{|W|^2} \quad (3)$$

where the calibration model W is, for example, a vector of regression coefficients and NAS is the net analyte signal. The net analyte signal is a figure of merit for systems involving multivariate calibration. A general definition of net analyte signal is the part of the measurement that is related uniquely to the variable of interest. Mathematically, the net analyte signal is the projection of the signal related to the analyte onto the null space of the interference. Net analyte signal is a portion of the analyte signal that is unique with respect to interference and is thus available for analyte detection and/or calibration use.

In a first embodiment of the invention, a model based upon a tissue phantom, a calibration data set, or a model parameter is used to determine instrument specifications, to assess analyzer performance, or to optimize processing procedures. One or more modifications of the in-vitro net analyte signal are used to determine the potential impact on measurement performance resulting from various instrument configurations and processing techniques. For example, a reduction in resolution is simulated by smoothing the net analyte signal according to a line-width function. This results in a rapid and cost effective method of determining the corresponding reduction in the signal to noise ratio or measurement performance. Similar analyses are performed to estimate impacts on a sampling interval, instrument noise, stray light, dispersion, device stability, alignment repeatability, and to perform a wavelength range optimization. For example, the net analyte signal is used to determine an optimal filter for application to in-vivo data which passes the signals with frequency characteristics similar to the net analyte signal while attenuating all other interference signals.

In-Vitro to In-Vivo

In a second embodiment of the invention, an in-vitro model is adapted to an in-vivo application. Adaptation of the in-vitro model to the in-vivo application preferably begins with the standardization of the in-vitro data set to the in-vivo instrument system. Alternatively, adaptation of the in-vitro model to the in-vivo application preferably begins with the standardization of the in-vivo instrument system to the in-vitro data set. For example, the resolution and wavelength sampling interval characteristics of the in-vivo apparatus are applied to the in-vitro data set through chemometric techniques, such as smoothing, interpolation, re-sampling, and/ or wavelength correction. Given the standardized in-vitro calibration set, an in-vitro model W is determined or a second in-vitro model is generated by modifying or standardizing a model directly. In a first case, the resulting the resulting model W is then applied to an in-vivo test set directly. In a second case, the resulting model W is then applied to an in-vivo test set with known glucose concentrations. The error in prediction is used to determine an offset, b, and/or a magnitude scaling factor a which is used to adjust the model for changes in the gross properties of the sampled matrix. For example, the magnitude compensates for pathlength differences associated with the sampling interface, as well as difference in the optical properties of the in-vitro and in-vivo samples. Glucose determinations are then performed according to equation 4, $$\hat{y} = xaW + b \quad (4)$$

where a is a scaling factor, b is the bias correction, x is a set of noninvasive spectral responses for a corresponding set of wavelengths, W is the model, and $\hat{y}$ is the estimated glucose concentration. In this circumstance the offset b is optionally periodically adjusted by repeating the determination of the offset. For example, periods of adjustment include: intra-day day, inter-day day, between use by separate subjects, between use on separate instruments, and/or between periods of time greater than a day. For example, the adjustment is the difference between $\hat{y}$ and the known or reference glucose concentration.

Standardization

Standardization is performed on either the calibration model or the data to which the model is applied. In either case, the objective is to enable the use of a calibration model that was developed from data collected on a different instrument or data set than the target instrument and data set. This is particularly useful in the case of calibration models that were developed, at least in part, based upon in-vitro data. Herein, calibration transfer is also referred to as standardization, standardizing, standardizing an instrument, or standardizing a model.

It is well known that identical performance of instruments is unrealistic, even with the successful implementation of tight quality control on instrument hardware. For example, variation in the output of a source, quality of lenses or mirrors, alignment, and detector response, which are limited by manufacturing tolerances, result in differences between spectrometers even of the same design. The instrument differences result in spectra of the father or master instrument varying from that of the daughter or slave instrument. It is well known that one or more calibrations developed on one or more instruments are often used on still additional instruments. Variations between the spectrometers result in errors when using a calibration developed on a first set of spectrometers to determine parameters with a second set of spectrometers. Generally, this error is increasingly detrimental as the signal-to-noise ratio of the determined analyte decreases. Processing and pre-processing is used with or without additional controls to adjust for differences in spectral response between the first and second set of spectrometers. This adjustment has developed into the field of calibration transfer. A number of calibration transfer or standardization techniques are known. Several representative techniques are described here.

Full recalibration of an analyzer is not preferable due to time requirements, technical expertise requirements, and expense. In addition, recalibration often fails to capture a full range of parameters, such as variations in the sample, environment, and instrument, thereby forcing additional recalibrations as the state of these parameters change. Calibration transfer is a standardization procedure designed to eliminate a full recalibration and to maintain information residing in the existing model. Calibration transfer is useful because in the development of the training (calibration) set sources of variation in the instrument, sample, and environment are modeled. Therefore, as the instrument, sample, or environment state changes the model components will not exactly match the current state. Broad models account for many changes. However, often changing parameters leads to an increase in estimation error or analyte determination.

Many areas are addressed in calibration transfer, such as wavelength (x-axis) stability, energy throughput (y-axis) stability, and bandwidth. Calibration transfers are used across time on one or more instruments, across many instruments of the same design, and across instruments of different design. Calibration transfer is also used when the sample varies. A living organism, such as the human body, undergoes continuous change. In addition, calibration transfers are used to adjust for changes in the environmental conditions, such as changes humidity or temperature.

Uses

Calibration transfer is used to compensate for changes to an x-axis. One approach to x-axis stability is to provide, with each sample or on a daily basis, spectra of a standard that is used to determine the x-axis. For adjustment of the x-axis in the near-infrared, polystyrene is often used. Additional near-infrared wavelength standards include rare earth oxides, such as holmium oxide, erbium oxide, and dysprosium oxide. Each standard or reference provides multiple peaks that are used to set or adjust the x-axis, such as a wavelength axis. In its broadest sense, any material that yields known or reproducible peaks for a given state is usable as an x-axis standard.

Calibration transfer is used to adjust or compensate for changes to a y-axis. For example, a y-axis is commonly adjusted with a reference standard. Examples of diffuse reflectance standards in the near-infrared include polytetrafluoroethylene diffuse reflectance standards, such as Labsphere™ (Labsphere, Inc., North Sutton, N.H.) diffuse reflectance standards that come with diffuse reflectances of 2, 5, 10, 20, 40, 60, 80, and 99%. Another approach is the use of standards that simulate the target sample, such as a tissue phantom or Intralipid. In its broadest sense, any material that yields known or reproducible transmittance, reflectance, or diffuse reflectance is usable as a y-axis standard.

Calibration transfer is used to adjust for variations in, between, or within a spectrometer. Calibration transfer is used to adjust for changes or differences in response, such as drift and shift. Drift is a slow, often continuous, change in instrument response. Shift is a sudden changes in instrument response. These effects are additive.

Sources of Variation

In near-infrared analyzers, there are many potential sources of variation in an analyzer, also known as a spectrometer.

A first source of variation is when there is a change in the entire spectrometer design. This is the case, for example, when a calibration is built on a first spectrometer, such as a master or a father spectrometer, and estimations (predictions) are performed on a different spectrometer, such as a slave or child spectrometer. This first type of variation is common when a research grade spectrometer is used for calibration and a process grade spectrometer, built with less stringent specifications, is used for subsequent analyses. As discussed above, even within a given spectrometer design, sources of variation exist. Variations exist even with tightly controlled manufacturing due to inherent manufacturing tolerances.

A second source of variation is a change in a part of a spectrometer. Examples of changing a part of a spectrometer include: changing a source, which can effect the blackbody radiation emitted; changing a monochromator or grating, which can effect the wavelength axis; changing a fiber optic or fiber bundle, which can effect the bandwidth; or changing the detector, which can affect the response curve or change a high or low frequency cut-off.

A third source of variation results from alignment of the spectrometer. Alignment changes result from movement of one or more of sub-components of the spectrometer. Alignment issues also result from mechanical design and fabrication.

A fourth source of variation is change in the environmental conditions about the spectrometer or analyzer. Common environmental changes affecting near-infrared spectra include temperature and humidity.

A fifth source of variation is change in the sample. Examples of changes in the sample include changes in chemical composition, sample finish, particle size distribution, and density. Examples of changes in a skin sample include changes in temperature, chemical composition, chemical distribution, physical structure, hydration, and/or localized pressure.

A sixth source of change are those associated with drift and offset, supra. In the near-infrared, sources of drift include source aging, optical alignment, temperature, and humidity. Sources of shifts, also known as rapid changes, include instrument component failure, entire instrument failure, and sample changes. Drift and offset changes are multiplicative.

In its broadest sense, the state of the spectrometer affects its output. Variation in state result in variation of output. For example, variation in state results in variation of the observed or calculated absorption coefficient and/or the observed or calculated reduced scattering coefficient. Calibration transfer is useful for adjusting for or compensating for the change in output resulting from change in state.

Techniques

There are many standardization or calibration transfer techniques, a number of which are reviewed here. Though these techniques are reviewed under the heading of calibration transfer, many of the techniques are useful in preprocessing or processing of spectra in the absence of calibration transfer.

One approach to calibration transfer is to generate a robust model that covers all future conditions. Experimental design is used to develop a robust calibration. E. Box, W. Hunter, and S. Hunter, *Statistics for experimenters*, Wiley-InterScience (1978) describe a variety of experimental design approaches. For noninvasive glucose concentration determinations, parameters include measurement conditions, such as temperature and humidity, as well as analyte/constituent concentration distributions. This approach is effective in controlled environments when the analyte signal-to-noise ratio is strong. However, the technique is not efficient in terms of time and money. Also, the quality of the calibration is suspect in terms of inability to predict future conditions that need to be incorporated into the original calibration. In addition, the technique does not readily allow incorporation of future conditions that are later identified without a new experimental design and development of a new or updated calibration.

A second approach is preprocessing the data or spectra. Typically, the same preprocessing is performed on data used to generate a calibration model and the data that the model is applied to. Generally, these techniques modify spectral response, such that spectra collected on different instruments are transformed so that the spectra appear as though they were all measured on the same instrument. However, identical preprocessing is not necessary. Common preprocessing techniques include: smoothing, performing a first derivative, performing a second derivative, applying multiplicative scatter correction, standard normal variate transformation (SNV), finite impulse response (FIR), and Fourier filtering. First derivatives are use to remove an additive effect, such as a baseline shift. Second derivatives are used to remove additive and multiplicative effects, such as a baseline slope. Multiplicative scatter correction (MSC) is used to simultaneously correct for additive and multiplicative effects in diffuse reflectance spectroscopy. M. Forina, G. Drava, C. Armanio, R. Boggia, S. Lanteri, R. Leardi, P. Corti, P. R. Giangiacomo, C. Galliena, R. Bigoni, I. Quartari, C. Serra, D. Ferri, O. Leoni, and L. Lazzeri, *Transfer of calibration function in near-infrared spectroscopy*, Chemometrics and Intelligent Laboratory Systems, 27, 189-203 (1995) and M. Dhanoa, S. Lister, R. Sanderson, and R. Barnes, *The link between multiplicative scatter correction (MSC) and standard normal variate (SNV) transformation of NIR spectra*", J. Near Infrared Spectrosc., 2, 43-47 (1994) describe standard normal variate transformation, which corrects for wavelength shifts and slope variation in spectra. T. Blank, S. Sum, S. Brown, and S. Monfre Transfer of near-infrared multivariate calibrations without standards, Anal. Chem., 68, 2987-2995 (1996) and S. Sum and S. Brown, *Standardization of fiber-optic probes for near-infrared multivariate calibrations*, Appl. Spect., 52, 869-877 (1998) describe finite impulse response, which uses a target spectrum, such as the mean of the calibration spectra. Transfer is performed by applying FIR filters to each individual spectrum from both the master and slave instruments, using the same spectral target. Different standards may be used for master and slave as long as they revolve around the same central space. Spectra of both the master and slave are filtered against the same reference spectrum. This approach effectively results in transfer of all spectra to a common reference without the requirement of transfer samples. M. Arnold and G. Small Anal. Chem., 62, 1457-1464 (1990) describe Fourier filtering, supra. The approach is to remove low frequency effects as in FIR as well as high frequency effects simultaneously. A very large number of additional preprocessing techniques are known in the art.

A third approach to calibration transfer is baseline correction, sometimes referred to as bias correction or offset correction. Bias correction corrects an estimated value Y according to equation 5 where $Y_{corr}$ is the corrected value, $Y_{pred}$ is the predicted or estimated value and offset is the bias.

$$Y_{corr} = Y_{pred} + \text{offset} \quad (5)$$

A slope/bias approach is also used to correct results. In this technique the slope of response is corrected at the same time as the offset. A benefit of this approach is that results are not damaged by artifacts, such as those resulting from bad local rank determination. These approaches are preferably used with master and slave spectra that are similar in nature obtained in similar conditions.

A fourth approach to calibration transfer is wavelength selection, whereby non-relevant information is removed. Wavelength selection is performed by testing against a monitoring or prediction set, by genetic algorithms, through simulated annealing, or by use of a-priori information, such as experience, basis set knowledge, or signal-to-noise ratios.

A fifth approach is to adjust the calibration model or to adjust the spectra. O. de Noord, *Tutorial multivariate calibration standardization*, Chemometrics and Intelligent Laboratory Systems, 25, p. 85-97 (1994), describes adaptation of calibration models. A selection of specific techniques are described below.

J. Shenk, O. Westerhaus, Optical instrument calibration system, U.S. Pat. No. 4,866,644 (Sep. 12, 1989); E. Bouveresse, D. Massart, P. Dardenne, *Calibration transfer across near-infrared spectrometric instruments using Shenk's algorithm: effects of different standardization samples*, Anal. Chim. Acta., 297, 405-416 (1994); and E. Bouveresse, E.; Massart, D. L.; Dardenne, P. *Modified algorithm for standardization of near-infrared spectrometric instruments*, Anal. Chem., 67, 1381-1389 (1995) describe what is commonly known as the Shenk algorithm. The Shenk algorithm performs both an x-axis and y-axis correction. For spectra, this is a correction to both wavelength axis and intensity or absorbance axis.

The Shenk algorithm is briefly described here in terms of x-axis and y-axis correction. In the x-axis correction, the standardization spectra are treated by a first derivative. For each standard and for each master wavelength (i) a spectral window (i−w to i+w) is chosen. The window is one or more wavelength wide. The correlations between the master and the slave spectra are computed. For each standard and for each master wavelength (i) a spectral window (i−w to i+w) on a slave is chosen. The correlations between $X_{mi}$, the master spectra, and $X_{si}$, the slave spectra, (from k=i−w to k=i+w) are computed according to equation 6.

$$R = \text{sqrt}((Am_{(i-2)} - AS_{(i+2)})^2 + \ldots + (Am_{(i+2)} - AS_{(i+2)})^2)/(2w+1) \quad (6)$$

The wavelength of highest correlation (m) is found. The wavelength axis shift is calculated with a linear model, with a quadratic, or higher order model. Using plot of corrected wavelengths on slave vs. original wavelengths on master, a quadratic best fit is obtained. Using a quadratic fit, the wavelengths of the slave i' are then related to the wavelengths of the master (i) via equation 7.

$$i' = A + B_i + C_i^2 \quad (7)$$

Interpolations are used to determine the intensity of the slave spectra at each wavelength (i).

The y-axis spectral intensity correction is obtained using linear regression of the responses of the slave instrument at each wavelength (i) of the shift corrected spectra, $X_{si}^{\#}$ on the response of the master instrument according to equation 8, $$X_{m_i} = a(i) + b(i) X_{S_{i_j}}^{\#} \quad (8)$$

where the intercept (a) and the slope (b) are computed for each wavelength (i). Wavelength by wavelength, the response of the slave is adjusted with the regression coefficients using equation 9, $$X_{std_i} = a(i) + b(i) X_{S_i}^{\#} \quad (9)$$

where $X_{std}$ is the $X_s$ matrix after standardization.

The Shenk algorithm has certain inherent difficulties. First, the correction fails for bandwidth corrections. Second, the method requires standards. The use of standards scanned on both the master and slave leads to problems as described, infra.

A sixth approach is to transform spectra collected on a slave instrument to appear as if they are collected on the master instrument.

Y. Wang, D. Veltkamp, B. Kowalski, Multivariate instrument standardization, Anal. Chem., 63, 2750-2756, (1991) describe a direct standardization (DS) technique. This technique relates all wavelengths on the slave to one wavelength measured on the master, as opposed to piecewise direct standardization (PDS), where a wavelength region (window) is related to 1-wavelength on the master. Direct standardization uses a subset of standards on both instruments. The subset selection must represent the data as closely as possible. A subset of samples can represent the standards or alternatively external standard are used. H. Swierenga, W. Haanstra, A. Weijer, L. Buydens, *Comparison of two different approaches toward model transferability in NIR spectroscopy*, Appl. Spect., 52, 7-16 (1998) describe PDS. If data are heterogeneous in the X-space, problems can occur with PDS. This is not an issue with slope/bias correction, which is based on the correction of the predicted values (Y-space) and is therefore not influenced by heterogeneity in the X-space. However, the primary difficulty of DS and PDS is finding these representative standards that must be stable and reproducible.

Interference Removal

A third embodiment of the invention compensates for one or more interferences. This embodiment is, optionally, performed after standardization as described in the second embodiment. For example, standardization techniques, such as resolution and wavelength sampling adjustments are performed prior to the interference compensation approach taught here. Given a calibration data set, or a standardized in-vitro calibration set, a second model $W_i$ is determined. The process of forming the second model is described, infra.

An interference model or interference basis set is created and associated with a new in-vitro application or to an in-vivo application. A basis set is one or more in-vivo spectra collected on the target apparatus platform. The basis set, optionally, includes a set of processed spectra that represents the expected detrimental in-vivo interference. Subsequently, the in-vitro net analyte signal is modified by removing the interference. This is accomplished by subtraction, as in equation 10, $$W_i = [I - x_b^T (x_b^T)^{-1}] W \qquad (10)$$

where, W is the initial model, I is an identity matrix, and $x_b^T$ is an interference. Mathematically, the regression vector of coefficients W is projected onto the null space of the interferences $x_b^T (x_b^T)^{-1}$ to form the second model. In a first case, null space interferences include chemical interferences, such as protein, fat, salt, thermal noise, or another chemical constituent of the sample. In this case, the second model $W_i$ is a new in-vitro model. In a second case, null space interferences $x_b^T (x_b^T)^{-1}$ represent a specific tissue sample, an individual, a class of subjects, or a cluster of data. The new model is either used directly or is further adapted. For example, further adaptation is achieved by applying the in-vivo model $W_i$ to an in-vivo test set with known glucose concentrations. The error in prediction is then used to determined an offset b and to magnitude adjust the model with a coefficient a. For example, the magnitude compensates for pathlength differences associated with the sampling interface as well as difference in the optical properties of the in-vitro and in-vivo samples. The new regression vector $W_i$ is applied to in-vivo spectra according to equation 11, $$\hat{y} = x a W_i + b \qquad (11)$$

where a is a scaling factor, b is the determined offset, and $\hat{y}$ is the analyte concentration, as described previously.

Additional methods of adaptation and standardization include multiplicative scatter correction, standard normal variate correction, and orthogonal signal correction. Optionally, the offset b is periodically adjusted using the comparison between $\hat{y}$ and the known or reference glucose concentration.

In yet another embodiment, an in-vitro data set is supplemented with in-vivo data. Adaptation of the in-vitro model to the in-vivo application is optionally performed. The original or standardized in-vitro calibration set is supplemented with in-vivo data from one or more subjects. The supplemented calibration set is used to determine a new calibration model associated with a particular subject and is, optionally, adapted over time through the addition of new data and calibration regeneration. Alternately, a standardized calibration is calculated through a larger calibration set including of standardized in-vitro and in-vivo data.

In yet another embodiment of the invention, a glucose tracking system is used. Referring now to FIG. 1, a glucose concentration tracking system (GTS) is presented. The system uses a glucose concentration analyzer that comprises at least a source, a sample interface, at least one detector, and an associated algorithm. Conventionally, all of the components of a noninvasive glucose analyzer are included in a single unit. In FIG. 1, an analyzer 10 is separated into elements including a base module 11, a communication bundle 12, and a sample module 13. The advantages of separate units are described, infra. The sample module, also referred to as a sampling module, interfaces with a tissue sample and at the same or different times with one or more reference materials. Herein, the combined base module 11, communication bundle 12, sample module 13, and algorithm are referred to as a spectrometer and/or analyzer 10. Preferably, the base module and sample module are in separate housings. Separate housing have benefits including: heat, size, and weight management. For example, the sample module is allowed to be smaller and weigh less without the bulk of the base module. This allows easier handling by the user and less of a physical impact on the sample site by the sample module. The sample module, base module, and communication bundle are further described, infra.

Sample Module

The sample module includes a sensor head assembly that provides an interface between the glucose concentration tracking system and the patient. The tip of the sample probe of the sample module is brought into contact with the tissue sample. Optionally, the tip of the sample probe is interfaced to a guide, such as an arm-mounted guide, to conduct data collection and removed when the process is complete. Guide accessories include an occlusion plug that is used to fill the guide cavity when the sensor head is not inserted in the guide, and/or to provide photo-stimulation for circulation enhancement. In one example, the following components are included in the sample module sensor head assembly: a light source, a single fiber optic, and coupling fluid. Preferably, the sample module is in a separate housing from the base module. Alternatively, the sample module is integrated into a single unit with the base module, such as in a handheld or desktop analyzer.

Communication Bundle

The communication bundle is a multi-purpose bundle. The multi-purpose bundle is a flexible sheath that includes at least one of:
  electrical wires to supply operating power to the lamp in the light source;
  thermistor wires;
  one or more fiber-optics, which direct diffusely reflected near-infrared light to the spectrograph;
  a tube, used to transport optical coupling fluid from the base unit, through the sensor head, and onto the measurement site;
  a tension member to remove loads on the wiring and fiber-optic strand from pulls; and
  photo sensor wires.

Preferably, the bundle has labeling instructions to the user to train the user not to twist the bundle and, optionally, mechanical means to prevent it from twisting more than one-quarter turn in either direction.

Base Module

A portion of the diffusely reflected light from the site is collected and transferred via at least one fiber-optic, free space optics, or an optical pathway to the spectrograph. The spectrograph separates the spectral components of the diffusely reflected light, which are then directed to the photodiode array (PDA). The PDA converts the sampled light into a corresponding analog electrical signal, which is then conditioned by the analog front-end (AFE) circuitry. The analog electrical signals are converted into their digital equivalents by the analog circuitry. The digital data is then sent to the digital circuitry where it is checked for validity, processed, and stored in non-volatile memory. Optionally, the processed results are recalled when the session is complete and after additional processing the individual glucose concentrations are available for display or transfer to a personal computer. The base module also, preferably, includes a central processing unit or equivalent for storage of data and/or routines, such as one or more calibration models or net analyte signals.

Permutation and combinations of the embodiments described herein are envisioned. For example, an interference removal is, optionally, performed in combination with a supplemental calibration.

EXAMPLE 1

The remainder of this specification provides an example of an in-vitro to in-vivo calibration transfer. A subset of this example has been presented in U.S. patent application Ser. No. 10/241,344, which is incorporated herein in its entirety by this reference thereto and in U.S. Pat. No. 6,475,800, which is incorporated herein in its entirety by this reference thereto. This example is illustrative of the invention and is not intended to limit the invention to the species presented.

Introduction

Diffuse-reflectance near-infrared spectroscopy is used to determine physiological concentrations of glucose in a novel tissue-simulating phantom. The tissue phantom, which is preferably composed of water and a modified form of Intralipid, is similar to skin of the human forearm in terms of its absorption coefficients and scattering properties. Additional key near-infrared absorbers of skin tissue in the 1000 to 2500 nm region are embodied in the phantom by the addition of glucose, albumin, and urea. Albumin and urea additives are, optionally, included as diluents that allow experimental designs ensuring that the glucose concentration is not correlated with time, any of the sample matrix constituents, or reference spectra. Using near-infrared spectra of the prepared samples and traditional chemometric techniques, glucose concentration determinations are subsequently demonstrated independently in the second overtone region (1025 to 1400 nm), first overtone region (1500 to 1840 nm), and combination band region (2025 to 2375 nm). These data and/or the associated models are used to estimate glucose concentration form in-vivo spectra.

Interpretation of noninvasive glucose concentration estimation models is complicated by both the dynamic nature of skin and multivariate analyses. Additionally, knowledge acquired from transmission studies is not sufficiently complete to allow deduction of fundamental concerns, such as the wavelength distribution of the photons as a function of both radius and depth, nor is it sufficient to allow adequate total optical pathlength analyses. In addition, some instrument parameters, such as resolution, required dynamic range, and skin sampling optics differ for a diffuse-reflectance-based glucose analyzer. Therefore, studies that are equivalent to the body of work performed in transmission mode addressing interferences, instrumentation parameters, sampling, and chemometric approaches are preferably completed using a diffuse-reflectance medium.

A suitable diffuse reflectance medium that allows these studies to be performed is generated. Several design criteria exist for the tissue phantom. First, the absorbance and reduced scattering coefficients of the tissue phantom preferably approximates that of human skin in the 1000 to 2500 nm spectral region. Second, the constituents of the tissue phantom preferably represent all major near-infrared absorbers in the skin. Third, interferences that are not present in the skin are preferably not introduced into the tissue phantoms. Fourth, a family of samples with quantitatively-known concentrations of all individual components is preferably created, such that the concentrations of the components within a study are decorrelated with respect to each other. Finally, the exact chemical and physical makeup of the sample is preferably known.

An excellent base scattering agent for building a novel family of samples is Intralipid™ (Kabi Pharmacia, Sweden), which is here briefly reviewed. Commercial Intralipid, manufactured by Kabivitrum (Stockholm, Sweden) and by Fresenius Kabi (West Clayton, N.C.), is a fat emulsion used clinically as an intravenous nutrient. Commercial Intralipid is made up of water, soybean oil, glycerol, and lecithin. Three forms of Intralipid are manufactured: 10%, 20%, and 30%, which refers to the soybean oil concentration. In commercially available Intralipid, only the concentration of the soybean oil varies with 100, 200, and 300 g/L in the 10%, 20%, and 30% solutions, respectively. The two other components, fractionated egg phospholipids and glycerol, remain constant in all varieties at 12 and 22.5 g/L, respectively. Thus, the ratio of the soybean oil to the other constituents is not fixed, indicating that literature values is interpreted based upon the stock Intralipid solution used.

In Intralipid, small soybean oil droplets are emulsified by lecithin monolayers to form scatterers. The mean size of the particles in Intralipid-10% is 1.00±0.14 µm, as measured by a coulter Counter. Freeze fracture studies by transmission electron microscopy excluding particles below 20 nm have yielded a smaller mean particle size of 97.3 with an exponential decrease in probability with increasing size reaching zero for a 700 nm diameter. These particles sizes indicate that 60 to 90% of the Intralipid soybean droplets are small enough to act as Rayleigh scatterers at the frequencies of interest from 1000 to 2500 nm. Emulsified particles are spherical with a form factor of 0.97; an ideal sphere has a value of 1. Form factors above 0.80 do not significantly influence Mie scattering calculations. This implies that the very slight nonspherical nature of the particles do not affect Mie scattering calculations.

The reduced scattering coefficient ($\mu'_s$), absorption coefficient ($\mu_a$), and anisotropy coefficient (g) of Intralipid are known in the visible and short wavelength region of the near-infrared. Inconsistencies in optical parameters are attributed to inconsistencies in the manufacturing process of the commercial Intralipid. Generally, the total attenuation coefficient and absorption coefficient decrease as the wavelength increases from 450 to 700 nm. Scattering dominates absorbance by a factor of 13,400 times at 633 nm. The anisotropy coefficient shows scatter to be primarily in the forward direction, falling from 0.88 at 450 nm to 0.72 at 1100 nm. At these longer wavelengths, the absorption coefficient is no longer dominated by the scattering coefficient and is preferably explicitly added to the models used to generate these coefficients.

It is demonstrated that modifications to commercial Intralipid result in a base scattering solution. Additional skin absorbers are, optionally, added to the solution to create a tissue phantom that models the near-infrared absorbance of human skin. This family of samples is based upon emulsions of oil in water with varying particle sizes using lecithin as the emulsifier. These solutions are, optionally, spiked with albumin, urea, and glucose to further simulate skin tissues. Other biological organic compounds, such as collagen, elastin, globulin, lactic acid, and bilirubin are optionally added to the family of samples. In addition, electrolytes are optionally added, such as $Na^+$, $K^+$, and $Cl^-$. Collectively, the resulting family of samples is known as Intra-serum. Layers of varying thickness having known index of refraction and particle size distributions are, optionally, generated using simple crosslinking reagents, such as collagen. The resulting samples are flexible in the concentration of each analyte and match the skin layers of the body in terms of their reduced scattering and absorption coefficients, $\mu'_s$ and $\mu_a$. This family of samples is provided for use in the medical field where lasers and spectroscopy-based analyzers are used in analysis and treatment of the body. In particular, applications are presented herein for the development of noninvasive glucose sensors using the near-infrared region from 1000 to 2500 nm.

Experimental Section

Two studies were run (Intra-serum 1 and Intra-serum 2), each with its own instrument configuration and corresponding spectral range. The apparatus, sample preparation, data collection, and processing procedures for each study are summarized in the following discussion.

Apparatus

In both studies, spectra were collected using a modified Nicolet Magna 860 (Madison, Wis.) spectrometer. For both studies, modifications of the Nicolet starting at the source and proceeding along the optical train to the detector are outlined here. The Intra-serum 1 data set used an Oriel model #66187 (Stratford, Conn.) auxiliary source housing, which was mechanically modified to couple into a Magna 860. The 600 W Oriel source was replaced with an L7390A, 100 W Gilway (Woburn, Mass.) tungsten-halogen source. A 2-inch diameter quartz plano-convex lens collimated the light, which was delivered into the Michelson interferometer of the Magna 860. The Intra-serum 2 data set used a customized auxiliary source accessory (ARA Engineering, Mesa, Ariz.). The Gilway source was again used. A spherical, concave backreflector with a 35-mm radius of curvature, 51.0-mm diameter, and 17.5-mm focal length was employed. A gold plated 38.1-mm focal length, 76.2-mm axial displacement off-axis parabolic reflector was used to collect the light and collimate it through the Michelson interferometer. Prior to the Michelson interferometer, an anti-reflective coated 1.075 and 1.450 µm longpass filter was employed between the source and the Michelson interferometer in the Intra-serum 1 and Intra-serum 2 studies, respectively. In both studies, the bench was configured with a $CaF_2$ beamsplitter. A 1-inch diameter 1-inch focal length sapphire lens, anti-reflection coated on both sides, positioned in the sample compartment coupled light into a custom-made 1 meter bifurcated fiber optic bundle (COLLIMATED HOLES, Campbell, Calif.). The fiber bundle consists of 261 close-packed, ultra-low-hydroxy 200 µm diameter silica input fibers with 240 µm silica cladding and 280 µm polyimide buffer. The sample interface is a rectangle of 37 fibers by 9 fibers. The reference standard was a 2% and 5% polytetrafluoroethylene diffuse reflectance standard in the Intra-serum 1 and Intra-serum 2 studies, respectively. The fiber bundle was inverted into a sample container with greater than 10 mm of Intra-serum in all directions from the fiber bundle tip. Seventy-two detection fibers are evenly intercalated within the excitation fibers. Collected light was focused through two 10-mm diameter 10-mm focal length sapphire lenses, which were anti-reflection coated on both sides, into a 2.6 µm 3-stage thermoelectrically-cooled InGaAs detector, operated at 7.375±0.125 kΩ (−19° C.). An OPA-627BM operational amplifier (Burr Brown) was used in the first gain stage of a preamplifier board, which coupled into the Nicolet amplifier board. The operational amplifier was configured with a 0.604 MΩ and 2.72 MΩ resistor in the Intra-serum 1 and Intra-serum 2 studies, respectively. The low pass filter capacitor was set at 5.5 kHz and the high pass filter was maintained at 1.5 kHz. The Nicolet was purged at a rate of 25 CFH at 25 psi with dried- and oil-free air from a Whatman 75-62 Fourier transform infrared air purifier.

Sample Preparation

Three stock solutions were analytically prepared with reagent grade Fisher Scientific™ (Pittsburgh, Pa.) chemicals: 4500 mg/dL 99.9% D-glucose, 624.99 mg/dL reagent grade urea, and 10000.04 mg/dL bovine serum albumin, Fraction V. Each of these three stocks was prepared with 0.483 g/L 5-fluorouracil. A fourth stock of 30% Intralipid was prepared by Fresenius Kabi (West Clayton, N.C.) without glycerol and was separated into 100, 100 mL intravenous bottles at time of preparation. A fifth stock of mega pure de-ionized water was generated as needed throughout the experiment.

The Intra-serum 1 data set included samples prepared from the stock solutions. Glucose concentrations ranged from 38.84 to 598.1 mg/dL, modified Intralipid from 2.99 to 8.00% by mass, urea from 4.80 to 69.78 mg/dL, and albumin from 492.7 to 2005 mg/dL. In Intra-serum 2, 152 samples were prepared. Glucose concentrations ranged from 38.20 to 601.5 mg/dL, modified Intralipid from 2.98 to 8.02%, urea from 4.81 to 70.4 mg/dL, and albumin from 494 to 2013 mg/dL. The samples were prepared with concentrations of each component (glucose, Intralipid, urea, albumin, and water) that are randomly correlated between samples. The samples were prepared gravimetrically using a micropipette to transfer varying amounts of each constituent's stock solution dropwise into a sample container; the mass was recorded after the addition of each stock. Sample concentrations were later calculated using the density of each solution. The order of addition of the stock was glucose, Intralipid, urea, albumin, and de-ionized water.

Data Collection

In the Intra-serum 1 data set, the Nicolet software was configured to collect single beam spectra from 11,000 to 3,500 $cm^{-1}$ (0.909 to 2.857 µm) at 4 $cm^{-1}$ (0.3 to 3.2 nm) resolution. In the Intra-serum 2 data set, the Nicolet software was configured to collect single beam spectra from 7,500 to 3,500 $cm^{-1}$ (1.333 to 2.857 µm) at 4 $cm^{-1}$ (0.7 to 3.2 nm) resolution. In both studies, 16 replicates with 128 co-added spectra per replicate were collected for each sample with a gain setting of one. Reference spectra were collected immediately prior to and after each sample. Spectra were triangularly apodized, Mertz phase corrected, treated with no zero filling, collected with a sample spacing of 1.0, subjected to an 11,000 Hz digital low-pass filter and a 200 Hz digital high-pass filter.

Processing

All subsequent processing of these data sets was performed using Matlab 5.2. Absorbance spectra were generated using the mean reference single beam spectrum. In each data set, the data was divided into calibration and prediction data sets. In the Intra-serum 2 data set, eight samples were removed due to an obvious specular reflectance term. Unless otherwise stated, all sixteen replicate sample spectra were co-added prior to analysis.

Results and Discussion

This data demonstrates the feasibility of glucose determination in diffuse reflectance mode in a tissue phantom using near-infrared spectroscopy from 1000 to 2500 nm. Further, this models generated from this data are used to demonstrate the prediction of noninvasive glucose from the forearm of an arm. Intralipid is chosen as the base diffuse-reflectance medium. Commercial Intralipid, however, has some undesirable absorbance bands. Therefore, Intralipid is initially broken down into its component parts. Constituents that yield absorbance and scattering characteristics matching human skin are retained, whereas those components that either serve no purpose in the phantom or are detrimental to the phantom are removed. Using the modified Intralipid, key near-infrared skin absorbers are then added to the matrix to create Intra-serum. Addition of albumin, glucose, and urea allow experimental designs where the concentrations of all individual components of the sample are quantitatively known and are preferably analytically varied within a study to decorrelate the concentration of each sample constituent with respect to the concentrations of other matrix components. A state-of-the-art near-infrared spectrometer is then used to collect spectra of the samples called for in the experimental design. Subsequent analysis is kept simple in order to clearly demonstrate glucose determination from the diffuse reflectance spectra.

Intralipid Modification

Figure 2:
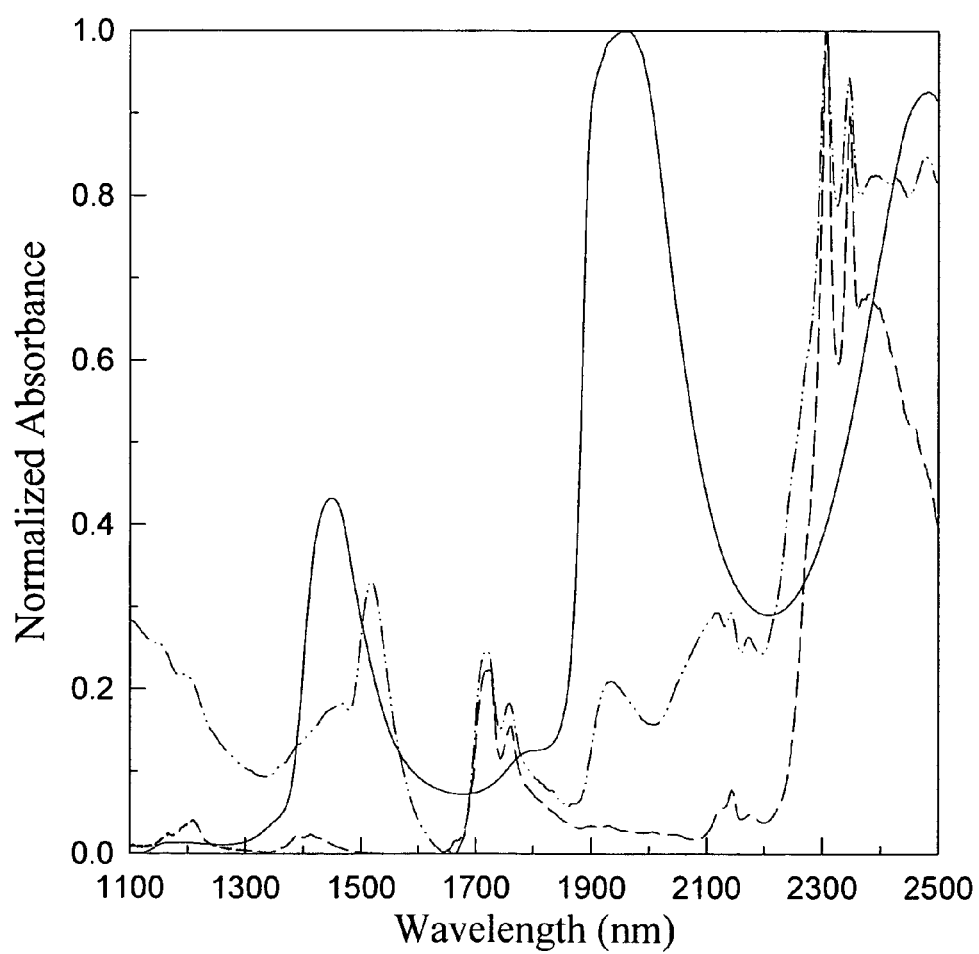
FIG. 2 presents normalized absorbance spectra of water, soybean oil, and lecithin used as interference spectra according to the invention.

The major component of Intralipid is water. Near-infrared absorbance of water has been well characterized and has strong absorbance bands at 1450, 1900, and 2600 nm, FIG. 2. As water makes up approximately 70% of skin tissue, inclusion of water in a matrix simulating the body is beneficial.

A second constituent of Intralipid is soybean oil. Soybean oil is made up of linoleic (44-62%), oleic (19-30%), palmitic (7-14%), linolenic (4-11%) and stearic acids (1.4-5.5%). These long chain oils simulate the long chain saturated and unsaturated fatty acid chains found in cell membranes and fat deposits within the body. Soybean oil has absorbance bands at 1167, 1210, 1391, 1413, 1724, 1760, 2123, 2144, 2307, 2347, and 2380 nm, FIG. 2. Every soybean oil band observed corresponds to a fat absorbance band in skin with the exception of the two absorbance bands near 1400 nm. These bands have not been observed in skin tissue due to the large interfering water absorbance band. Notably, the soybean oil absorbance bands are red-shifted relative to the short carbon chain triacetin absorbance bands. For solubility reasons, triacetin has been used to simulate fat in earlier serum phantoms. A second major benefit of soybean oil is that within Intralipid, the oil has been homogenized into small droplets. The scattering nature of these droplets was reviewed in the introduction for the visible and therapeutic regions. The scattering nature of Intralipid has been separately reported in the near-infrared region from 1000 to 2500 nm. The observed absorbance of soybean oil and the reported scattering characteristics of Intralipid make soybean oil a valuable constituent of the tissue phantom.

An additional constituent of Intralipid is lecithin, a phosphatidylcholine. The zwitterion nature of the choline ester allows lecithin to act as an emulsifier, forming a monolayer around small oil particles that results in near-IR scatterers. Fat emulsions made of soybean oil and emulsified by egg phosphatides are exclusively composed of long-chain triglycerides. An absorbance spectrum of a 10% lecithin, 90% KBr crushed pellet collected in transmission mode demonstrates that the primary absorbance bands of lecithin match those of soybean oil, FIG. 2. This is expected since lecithin is a mixture of the diglycerides of stearic, palmitic, and oleic acids, which are the primary constituents of soybean oil. Additional absorbance bands observed at 1518 and 1938 nm are likely to be due to the choline ester.

The observed absorbance of lecithin increases from 1300 to 1100 nm due to scattering of light. Approximately half of the lecithin is used to coat soybean oil droplets in Intralipid-10%. Centrifugation studies show that one-third of the lecithin is used to coat the oil in Intralipid-10% and two-thirds is used to coat the oil in Intralipid-20%. These later numbers support the total amount of lecithin used in the Intralipid-30%. Because lecithin has two fatty acid acyl chains, steric effects prevent the formation of micelles. Therefore, the excess insoluble lecithin swells to form a colloidal suspension of small bilayer vesicles that scatter light. In independent studies, increased scattering of light has been observed in lecithin and water mixtures as the lecithin concentration increases. This phenomenon has not been included in any of the scattering models on commercial Intralipid in the literature. Lecithin is considered a useful element of a tissue phantom because it creates scattering droplets with soybean oil, it occurs naturally in all living organisms, and it has absorbance bands in the same location as body fat.

The final component of commercial Intralipid is glycerol ($C_3H_8O_3$) or 1,2,3-propanetriol, which is miscible with water and has a concentration in Intralipid of 1.8%. Glycerol has absorbance bands at 1626, 1689, 1732, 2105, 2272, and 2326 nm. Glycerol at 1.8% has absorbance bands that correspond in position and magnitude to glucose at a concentration of approximately 3000 mg/dL. Near-infrared analysis of glucose with diabetic physiological ranges of 30 to 700 mg/dL in the presence of varying amounts of glycerol using standard chemometric techniques is difficult. Because glycerol is miscible in water, it does not form particles of scattering dimensions in the near-infrared region and since glycerol has an index of refraction of 1.4730 that is reasonably matched to water, glycerol does not contribute significantly to the scattering of the solution. Furthermore, glycerol contributes insignificantly to the overall absorbance of Intralipid compared to water, soybean oil, and lecithin. In addition, glycerol is not a major constituent of skin or blood. Finally, glycerol is present in Intralipid as a nutrient; however, it is not necessary in the tissue phantom. For these reasons, glycerol is not a preferable constituent of a diffuse reflectance tissue phantom. The modified Intralipid stock used in these studies was prepared without glycerol.

Tissue Phantom Preparation

Figure 3:
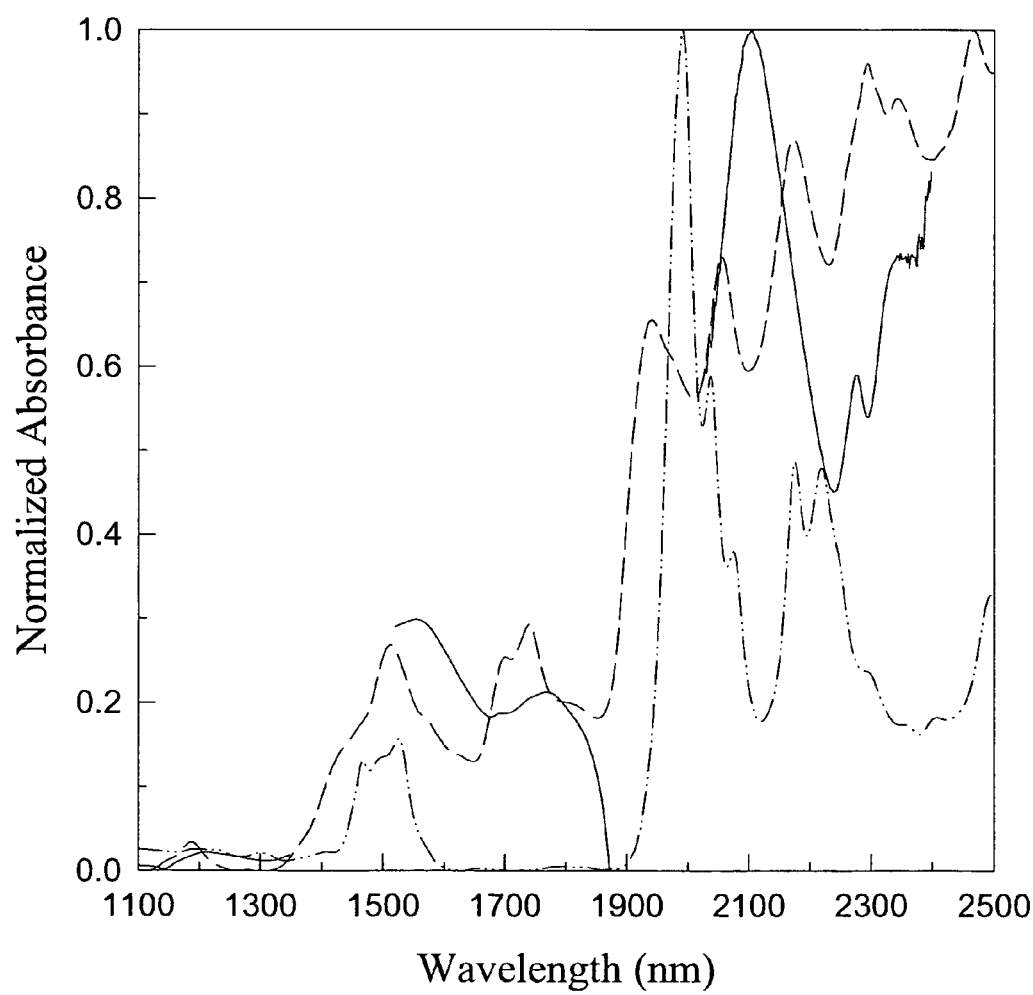
FIG. 3 presents normalized absorbance spectra of albumin, urea, and glucose used as interference spectra according to the invention.

Noninvasive near-infrared diffuse-reflectance spectra of skin have a number of large spectral features. The two strongest are the water absorbance bands and scattering effects leading to a number of spectral features including variations in pathlength with wavelength. Spectra of the modified Intralipid matrices model these parameters. However, skin and blood contain several additional near-infrared absorbers that behave as interferences in glucose determinations. Collagen and elastin proteins are present in skin. Collagen makes up approximately 75% of the dry weight of skin and elastin is the next largest component. Additionally, albumin and globulin protein are the primary constituents by mass in blood. Albumin, globulin, collagen, and elastin have similar absorbances in the near-infrared since they are all proteins. Because albumin is soluble in water, it is selected to be included in the tissue phantom as an interfering constituent simulating the skin proteins, FIG. 3. A smaller near-infrared skin absorber is urea, which has absorbance bands in the combination band and second overtone spectral regions. Addition of urea to the tissue phantom acts as an additional interference as well as a diluent. Finally, glucose is added into the Intra-lipid matrix as the analyte.

Figure 4:
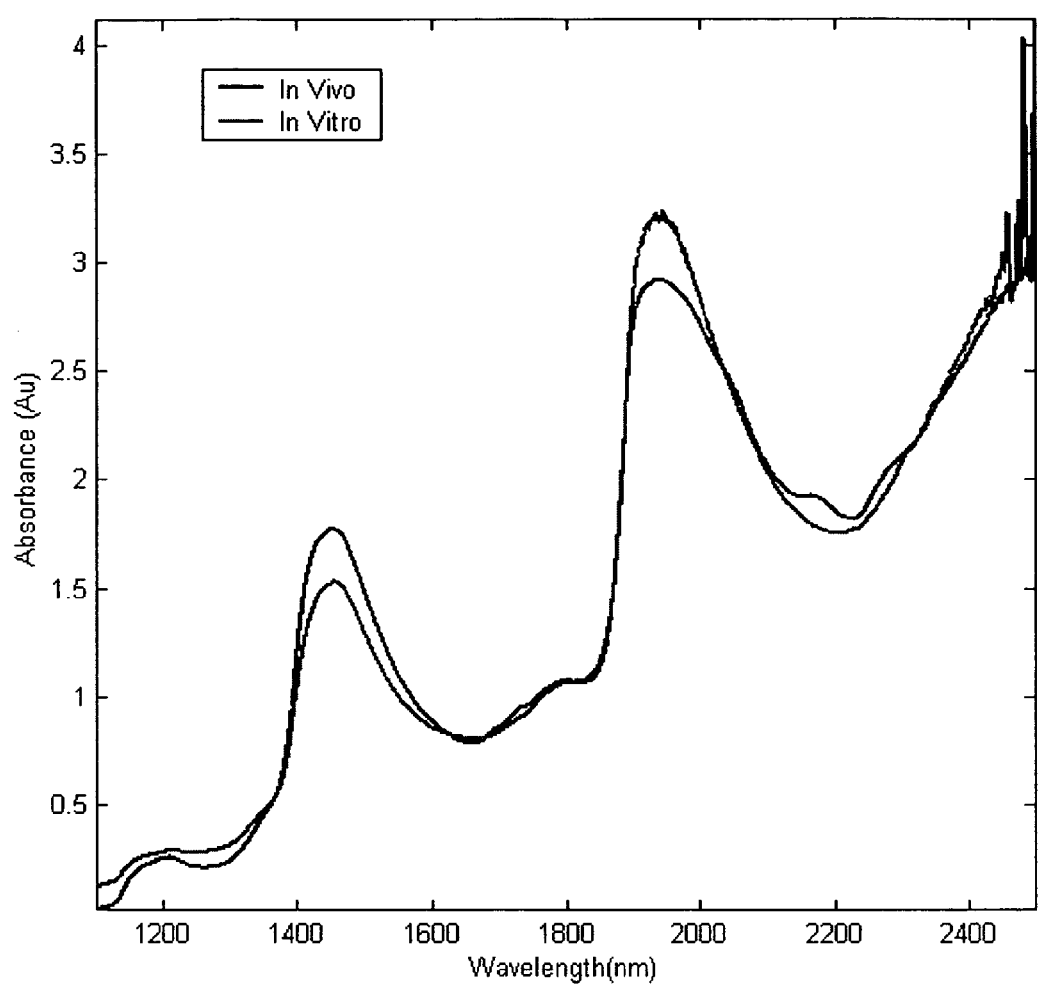
FIG. 4 presents a noninvasive spectrum of a human forearm and a diffuse reflectance spectrum of an in-vitro sample used to model the tissue according to the invention.

Modified Intralipid and water are optionally combined to form tissue phantoms with a reduced scattering coefficient to absorbance coefficient ratio ($\mu'_s/\mu_a$), simulating those of skin. The family of samples consisting of water, soybean oil, lecithin, albumin, urea, and glucose is referred to as Intra-serum. Water is the primary absorber of Intralipid, and the emulsified soybean oil droplets are the primary scatterers in the Intra-serum samples. A spectrum of Intra-serum is shown in FIG. 4 along with a non-invasive spectrum of the arm. The absorbance of the Intra-serum is slightly higher than that of the arm in the combination band (2000 to 2500 nm) and slightly lower than the arm in the second overtone region (1000 to 1450 nm), but closely matches the absorbance of the arm in the first overtone spectral region (1450 to 2000 nm). Most of the absorbance bands present in the skin are identified in the Intra-serum sample, with the exception of the protein bands in the first overtone and combination band regions. The maximum concentration of protein in the Intra-serum is 2000 mg/dL, more closely matching the true albumin concentration of blood. In contrast, the tissue phantom does not optimally model the deeper adipose fat absorbance bands of the second overtone. The soybean oil-based Intralipid is a close approximation, but not a perfect one, due to the slight scattering differences seen between the arm and the Intra-serum. An Intralipid with a greater mean particle size is, optionally, used to provide increased scattering at longer wavelengths and to decrease the scattering at shorter wavelengths.

The Intra-serum samples have absorption and reduced scattering coefficients approximating those of skin tissue. In addition, the combination of water, modified Intralipid containing long chain fatty acids, albumin, urea and glucose represent all of the major near-IR absorbers of blood and of skin tissue. Finally, the concentration of each constituent is, optionally, varied independently from sample to sample. Combined, these attributes enable the creation of a family of samples that allows for the feasibility testing of noninvasive diffuse reflectance near-infrared determinations of glucose concentration.

Experimental Design

The Intra-serum samples are composed of water, Intralipid (soybean oil, lecithin and water), albumin, urea, and glucose. If only glucose and Intralipid are present, the Intralipid concentration is inversely correlated with any change in the glucose concentration. The addition of multiple constituents allows the glucose concentration to be uncorrelated with all other sample constituents allowing for critical interpretation of multivariate analysis of the subsequent spectral data sets. The albumin concentration is kept low and the urea concentration is high, allowing further decorrelation of the concentrations of the components in the experimental design.

The experimental design included the formation of a 4-dimensional data cube with the axes defined by the desired concentrations of the modified Intralipid, albumin, urea, and glucose. The cube was subdivided into 108 sub-cubes. One sample was prepared for each sub-cube, with the concentrations of each constituent being randomized within each sub-cube. Finally, spectra of the resulting samples are collected in a random order versus time. This process ensures that the glucose concentration and the concentrations of all additional sample constituents are random with respect to time. Again, this random variation is designed into the data sets due to the inability of multivariate analysis techniques to separate causes of spectral variation. The correlation coefficients of each Intra-serum constituent versus sample number (time) and versus all other sample constituents are summarized in Table 1. All correlation coefficients are below 0.1, indicating extremely poor correlations between analytes.

TABLE 1

Correlation of Sample Constituents with Each Other and with Time

| Intra-serum 2 | Intra-serum 1 | | | | |
|---|---|---|---|---|---|
| | Time | Intralipid | Albumin | Urea | Glucose |
| Time | N/A | −0.0463 | 0.0054 | −0.0354 | −0.0013 |
| | | 0.0133 | 0.0411 | −0.0301 | −0.0334 |
| Intralipid | −0.0463 | N/A | −0.0519 | −0.0376 | 0.0637 |
| | 0.0133 | | 0.0804 | 0.0629 | −0.0031 |
| Albumin | 0.0054 | −0.0519 | N/A | −0.0014 | 0.0076 |
| | 0.0411 | 0.0804 | | −0.1930 | 0.0311 |
| Urea | −0.0354 | −0.0376 | −0.0014 | N/A | −0.0979 |
| | −0.0301 | 0.0629 | −0.1930 | | 0.0212 |
| Glucose | −0.0013 | 0.0637 | 0.0076 | −0.0979 | N/A |
| | −0.0334 | −0.0031 | 0.0311 | 0.0212 | |

Instrumentation/Spectra Characterization

As detailed in the experimental section, a modified Nicolet 860 Fourier transform based spectrometer is used in these studies. A customized auxiliary source is optically coupled to a customized fiber optic interface, which in turn is coupled to the sample. The fiber bundle interface with the sample eliminated the specular reflectance term. Combined, these allow a high throughput, high resolution, low noise and fast data acquisition spectrometer.

Intensity

Use of the 1450 nm longpass filter eliminated signal in the $2^{nd}$ overtone region in the Intra-serum 2 data set, which allows the dynamic range of the Nicolet to be freed for the detection of signal in the $1^{st}$ overtone and combination band regions. As the dynamic range was filled in the Intra-serum 2 study, an increase in peak intensity of the $1^{st}$ overtone and combination band regions of 382% and 524%, respectively, is observed relative to the Intra-serum 1 study. The larger gain in the combination band region is due to the removal of the quartz optic in the auxiliary source. The inset shows the peak $1^{st}$ overtone intensity for the six Intra-serum samples at 1678 nm. The nonlinear nature is expected in a scattering medium and typically leads to additional factors being required with the linear partial least squares (PLS) analyses that follow.

Signal

A pure component spectrum of glucose is generated using multivariate curve resolution. Glucose and water spectra were collected in transmittance mode with a 1-mm pathlength with glucose concentrations ranging from 0 to 15,000 mg/dL at 1000 mg/dL intervals. Using this data, a calculated pure component glucose spectrum is generated, FIG. 3. The gaps in the resulting spectrum are where the large water band led to unacceptable certainty of the glucose spectrum. The resulting spectrum was verified using multivariate curve resolution on data sets using multiple analytes, with different spectrometers and with varying detectors. Notably, the signal strength for a fixed pathlength is largest in the combination band region, roughly a third the strength in the first overtone region, and small but identifiable in the second overtone region.

Noise

A criterion for interpretation of near-infrared glucose analysis is the spectrometer noise level. Noise is estimated as the root mean square of successive reference spectra collected throughout the studies. The intensity is the mean single beam spectrum in each of the Intra-serum studies. As expected, the resulting noise levels are proportional to the absorbance of water. The instrumentation used in the Intra-serum 2 study yields lower noise levels as is expected from the increased signal levels made possible with the 1.450 μm longpass filter. Noise levels of less than 10 micro-absorbance units are generated in the second overtone and $1^{st}$ overtone regions. In the combination band region, noise levels increase towards 100 micro-absorbance units. After adjusting for the net pathlength as a function of frequency, these noise levels are on the order of the signal level for glucose in the first and second overtone regions and are restrictive in the combination band region.

Multivariate Analysis

There is a risk of multivariate models improperly reporting glucose concentration estimation where the actual spectral signatures modeled are instrument variations correlating to the actual glucose concentrations. This risk is overcome by an experimental design that forced all samples constituents to be random versus time. Two tests confirm this. First, the reference spectra collected with each sample are substituted for the sample spectra with the same preprocessing and spectral ranges as used to determine glucose concentrations. For each spectral range analyzed, prediction errors of roughly 155 and 177 mg/dL are achieved for the Intra-serum 1 and 2 data sets, respectively. These prediction errors are equal to the standard deviations of the actual glucose concentrations in the two prediction data sets of 156.5 and 178.8 mg/dL, respectively. This strongly indicates that the multivariate PLS algorithm is not modeling any instrument variation. Additionally, the resulting f-test values indicate that the reference spectra can't be used to determine the glucose concentrations at the 90% confidence level ($F_{90}$=1.70). These tests on the reference spectra clearly demonstrate that variations in the spectrometer are not being used to determine the glucose concentrations. In the same way that randomization of the sample concentrations with time leads to the ability to rule out spectrometer drift, all parameters that change with time, such as systematic degradation of the samples or variations in room temperature, are disregarded despite having no direct measurement of these parameters.

The data set from Intra-serum 1 is broken into two subsets. The calibration subset is the first 97 samples, which represents 1552 spectra and 75% of the data. The prediction subset is the last 30 samples that represents 480 spectra and 25% of the data. The correlation between sample constituents was found to be minimal and therefore not a source of confusion in subsequent multivariate analyses, Table 2.

TABLE 2

Correlation Coefficients of each Sample Constituent with additional Sample Constituents

| Prediction | Calibration | | | |
| --- | --- | --- | --- | --- |
| | Intralipid | Albumin | Urea | Glucose |
| Intralipid | N/A | 0.0004 | 0.0049 | 0.0064 |
| | 0.04 | 0.0009 | 0.0441 |
| Albumin | 0.0004 | N/A | 0.0016 | 0.0016 |
| | 0.04 | | 0.0169 | 0.0049 |
| Urea | 0.0049 | 0.0016 | N/A | 0.0081 |
| | 0.0009 | 0.0169 | | 0.0016 |
| Glucose | 0.0064 | 0.0016 | 0.0081 | N/A |
| | 0.0441 | 0.0049 | 0.0016 | |

A principal component analysis of the Intra-serum 1 data set was performed. An explanation of variance for the model is presented in Table 3. The standard error of the calibration and independent prediction shows a classic decrease in error after the initial factors. From this, it is observed that principal components six and ten lead to the largest individual decreased in the standard error of prediction. Combined, the two factors account for 77% of the explained glucose composition.

TABLE 3

Variance Model
Percent Variance Captured Error

| | X-Block | | Y-Block | | | |
| --- | --- | --- | --- | --- | --- | --- |
| LV # | This LV | Total | This LV | Total | SEC | SEP |
| 1 | 99.46 | 99.46 | 0.82 | 0.82 | 173.74 | 180.22 |
| 2 | 0.35 | 99.81 | 0.07 | 0.89 | 173.73 | 179.89 |
| 3 | 0.08 | 99.89 | 1.64 | 2.53 | 172.35 | 177.59 |
| 4 | 0.05 | 99.94 | 2.12 | 4.65 | 170.52 | 171.02 |
| 5 | 0.03 | 99.98 | 0.00 | 4.65 | 170.57 | 170.98 |
| 6 | 0.01 | 99.99 | 64.19 | 68.83 | 97.55 | 96.16 |
| 7 | 0.00 | 99.99 | 9.78 | 78.61 | 80.84 | 78.32 |
| 8 | 0.00 | 99.99 | 0.92 | 79.53 | 79.11 | 79.79 |
| 9 | 0.00 | 100.00 | 0.18 | 79.71 | 78.79 | 79.04 |
| 10 | 0.00 | 100.00 | 13.27 | 92.98 | 46.35 | 43.96 |
| 11 | 0.00 | 100.00 | 2.15 | 95.14 | 38.60 | 39.99 |
| 12 | 0.00 | 100.00 | 0.14 | 95.27 | 38.06 | 38.12 |
| 13 | 0.00 | 100.00 | 0.09 | 95.36 | 37.72 | 38.65 |
| 14 | 0.00 | 100.00 | 1.40 | 96.76 | 31.52 | 32.61 |
| 15 | 0.00 | 100.00 | 0.03 | 96.79 | 31.40 | 31.65 |
| 16 | 0.00 | 100.00 | 0.02 | 96.81 | 31.33 | 31.63 |
| 17 | 0.00 | 100.00 | 0.08 | 96.89 | 30.94 | 31.89 |
| 18 | 0.00 | 100.00 | 0.22 | 97.10 | 29.85 | 31.06 |
| 19 | 0.00 | 100.00 | 0.20 | 97.31 | 28.78 | 29.99 |
| 20 | 0.00 | 100.00 | 0.00 | 97.31 | 28.78 | 29.87 |
| 21 | 0.00 | 100.00 | 0.02 | 97.33 | 28.67 | 29.82 |
| 22 | 0.00 | 100.00 | 0.18 | 97.51 | 27.71 | 29.42 |
| 23 | 0.00 | 100.00 | 0.01 | 97.52 | 27.66 | 29.38 |
| 24 | 0.00 | 100.00 | 0.08 | 97.60 | 27.20 | 29.33 |
| 25 | 0.00 | 100.00 | 0.00 | 97.60 | 27.21 | 29.32 |

Figure 5:
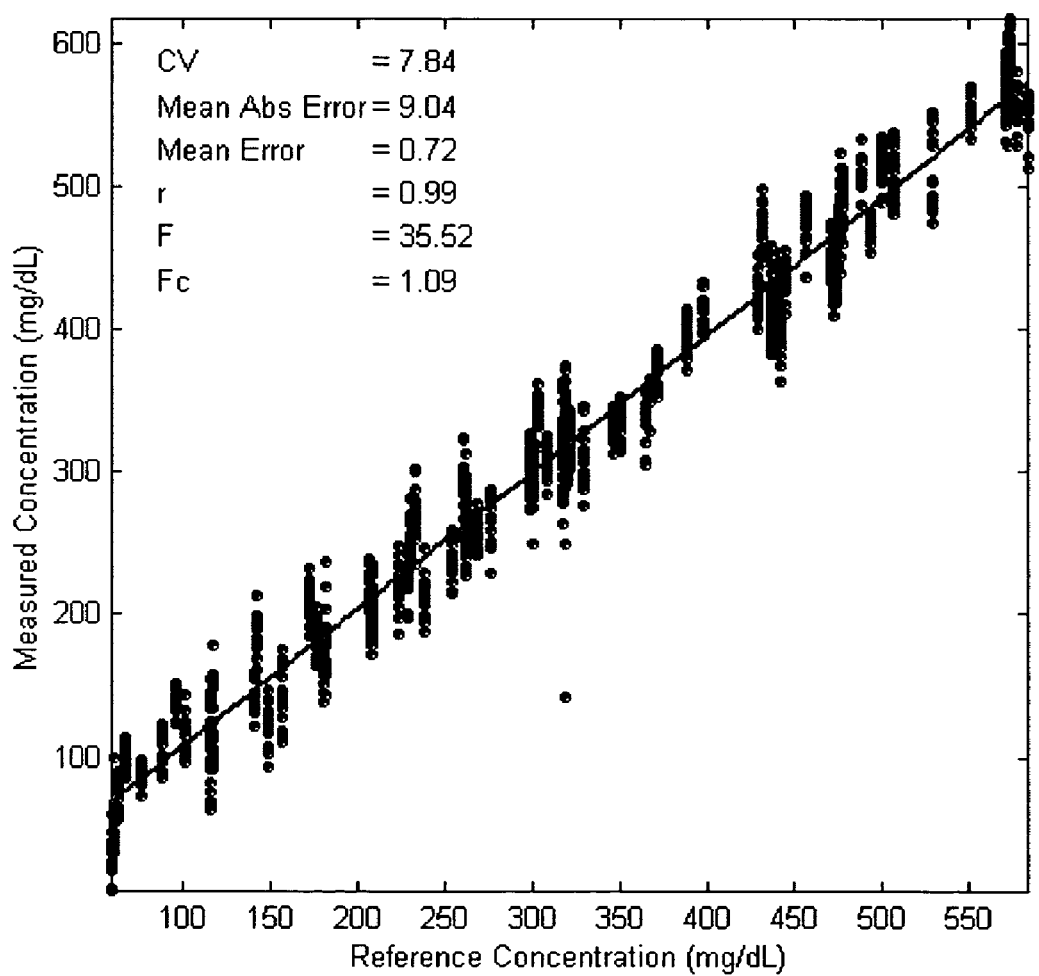
FIG. 5 presents a concentration correlation plot for the calibration data corresponding to the 22-factor model according to the invention.
Figure 6:
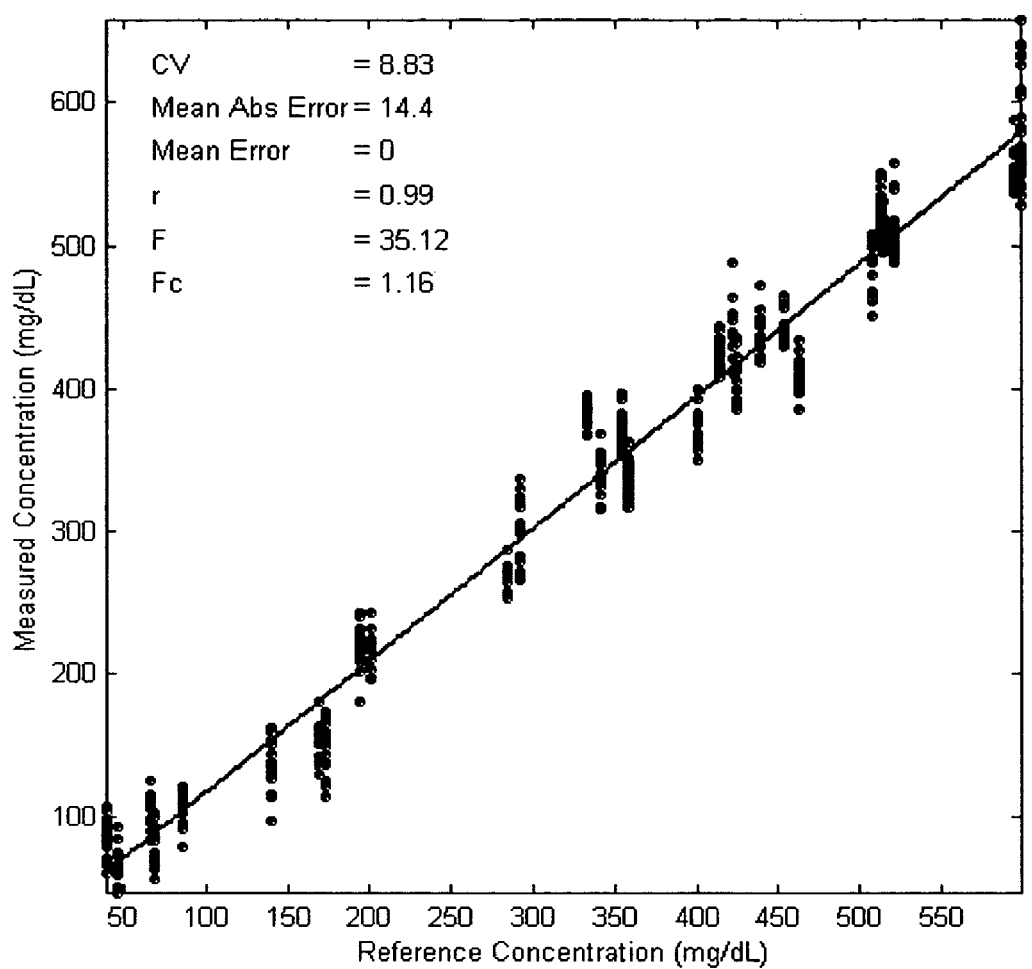
FIG. 6 presents the corresponding concentration correlation plot for the prediction data after application of the 22-factor model according to the invention.

The calibration and prediction concentration correlation plots for the 22 factor model are presented in FIGS. 5 and 6, respectively. No bias is observed with respect to the reference method. As with all models examined herein, the error does not increase at lower glucose concentrations, which indicates that random noise is not the limiting criterion for glucose determination in these data sets. This agrees directly with the significantly larger single beam intensity in the first overtone region of the Intra-serum 2 data leading to only a minor reduction in the resulting standard error of prediction.

Figure 7:
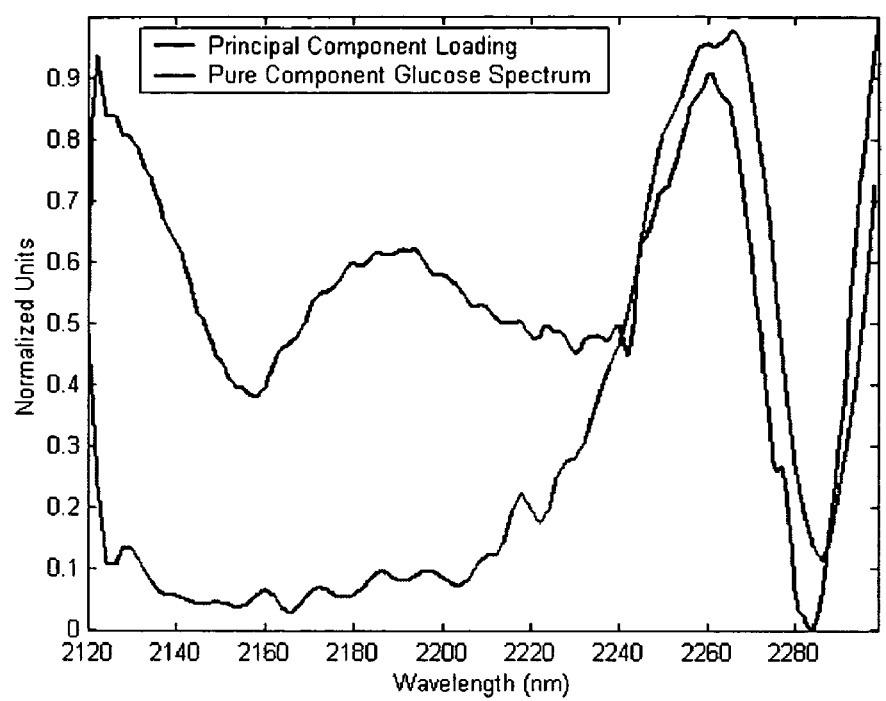
FIG. 7 presents the sixth loading overlaid with a pure component glucose spectrum in the combination band region according to the invention.
Figure 8:
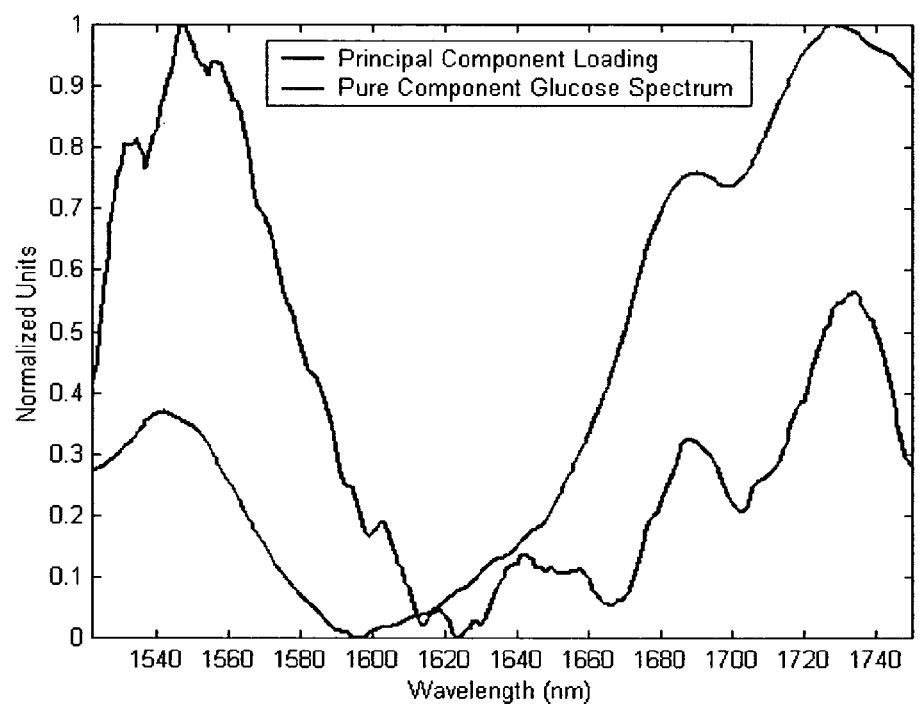
FIG. 8 presents the tenth loading overlaid with a pure component glucose spectrum in the first overtone region according to the invention.

Further evidence that glucose is being modeled is provided by analysis of spectral loadings. The sixth principal component is overlaid with a pure component glucose absorbance band in FIG. 7. This analysis shows a high correlation with the glucose band at 2350 nm. The tenth principal component is overlaid with a pure component glucose absorbance band in FIG. 8. This analysis shows a high correlation with the glucose absorbance bands at 1550, 1680, and 1720 nm.

Additional analysis, not presented here, indicates that glucose concentration predictions are achieved independently in each of the second overtone, first overtone, and combination band spectral regions. Combining the first overtone and combination band regions failed to reduce the standard error of prediction of glucose concentration in the Intra-serum 2 data set, due to the high noise levels observed in the combination band region. Combining the second overtone region to the first overtone region in the Intraserum 1 data set lead to a 50% reduction in the standard error of prediction of glucose concentration. This result indicates that the primary glucose information is in the first overtone spectral region, but that a combination of regions is helpful.

Regression Analysis

Figure 9:
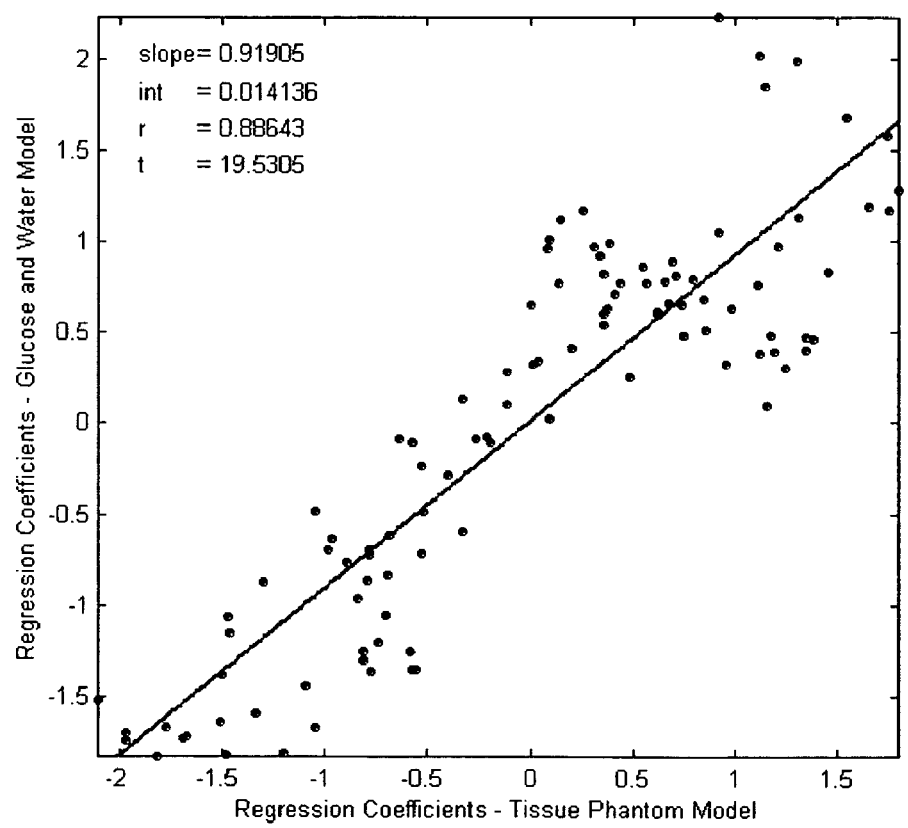
FIG. 9 presents a correlation plot comparing the regression coefficients of a glucose in water model with that of a tissue phantom model according to the invention.

A regression vector was generated from a glucose in water data set. The resulting regression vector is compared with the regression vector generated from the Intra-serum 1 data set in FIG. 9. After scaling and filtering to remove high frequency content, it is observed that the water and tissue phantom regression vectors are highly correlated. This is evidence of glucose being modeled in the tissue phantom.

Figure 10:
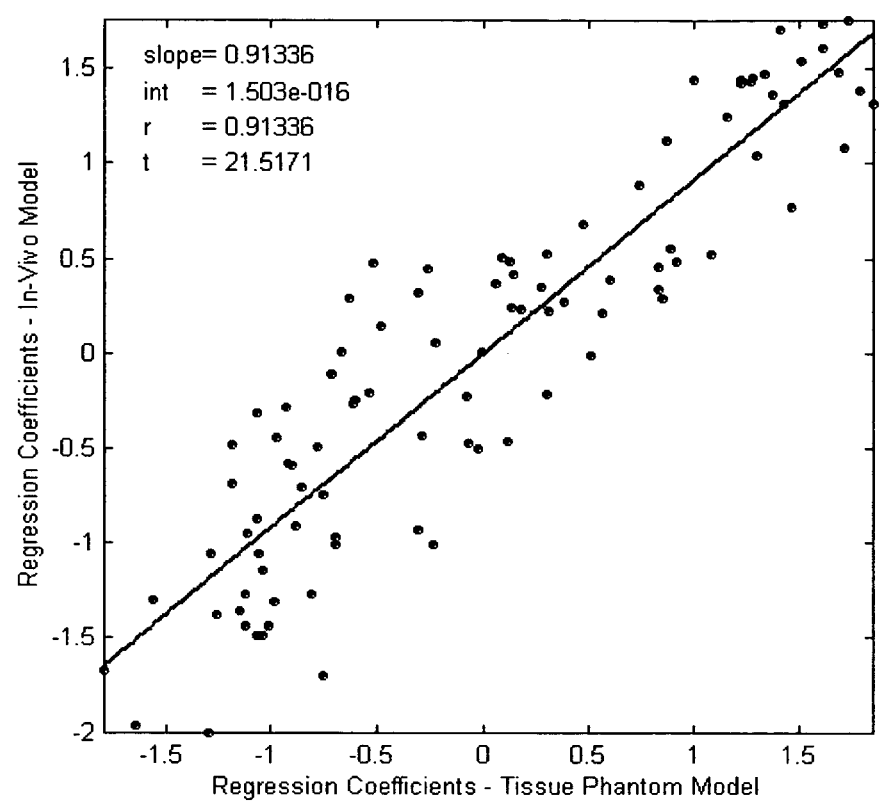
FIG. 10 presents a correlation plot comparing the regression coefficients of a noninvasive model with that of a tissue phantom model according to the invention.

Similarly, a regression vector was generated from a noninvasive data set. The resulting regression vector is compared with the regression vector generated from the Intraserum 1 data set in FIG. 10. After scaling and filtering to remove high frequency content, it is observed that the two regression vectors are highly correlated. This is evidence of glucose being modeled in the tissue phantom. Analysis of the spectral variance and principal component scores confirms that the net analyte signal is related to the absorbance due to glucose.

Figure 11:
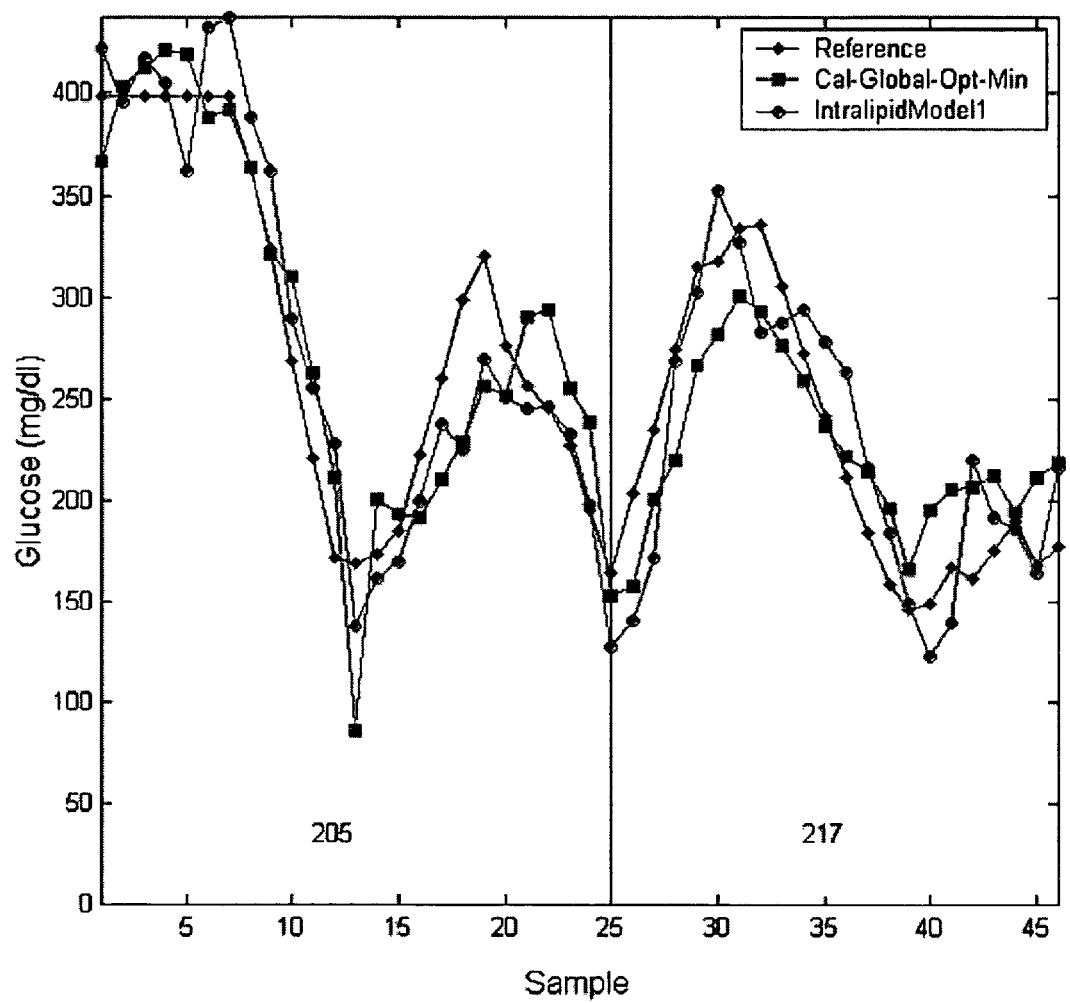
FIG. 11 shows a in-vitro model predicting glucose concentrations as well as an in-vivo model according to the invention.

Several examples follow that show the use of the in-vitro model to predict accurately and precisely predict glucose from noninvasive measurements. Initial work is presented in FIG. 11. FIG. 11 demonstrates in a time-series glucose profile analysis that the in-vitro model is performing in a fashion similar to that of the in-vivo model. This is remarkable considering that the in-vitro data was collected on a Fourier transform based spectrometer, using prepared samples, in-vitro, years prior to the analysis of the in-vivo data. Further, the in-vivo data optimized for the glucose analyzer platform that in this case is array based.

Figure 12:
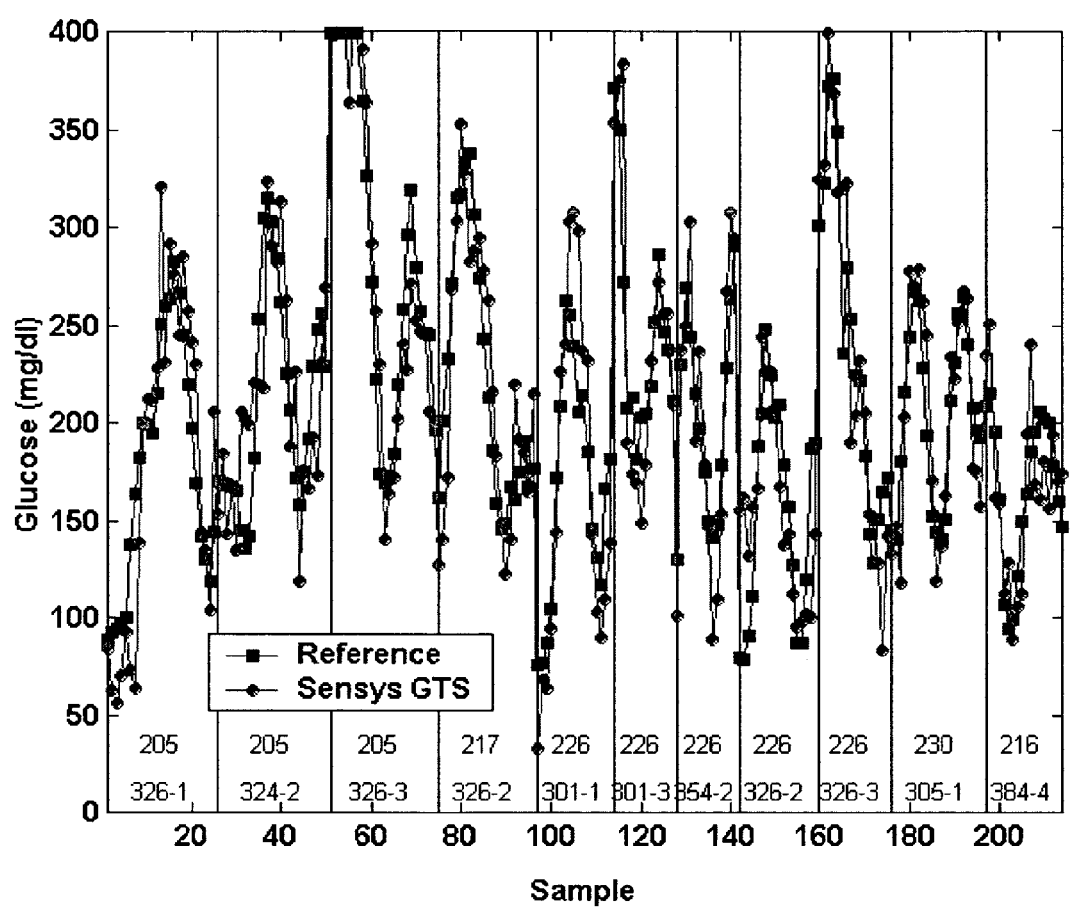
FIG. 12 presents in-vitro model predictions that closely track traditional invasive glucose concentration determinations according to the invention according to the invention.
Figure 13:
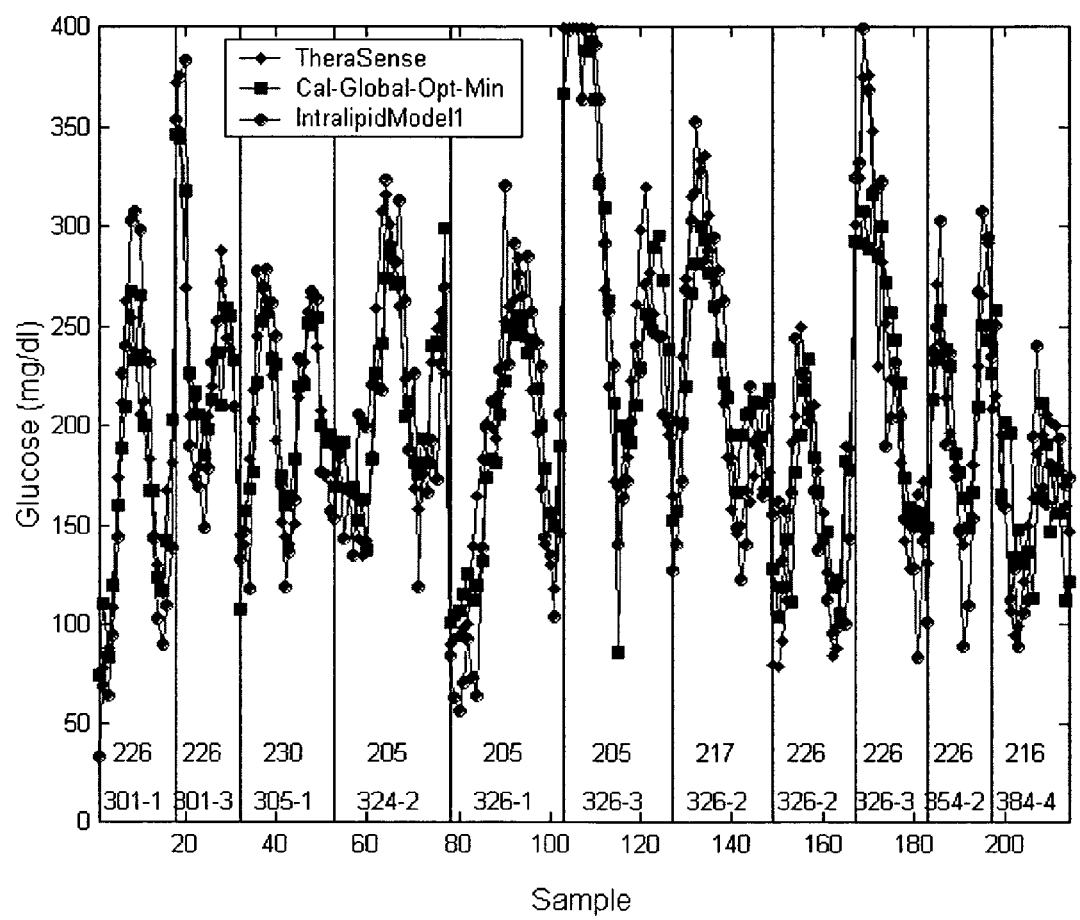
FIG. 13 presents in-vitro model predictions that track traditional invasive glucose concentration determinations as well as an in-vivo model according to the invention.

More recent work clearly shows that the in-vitro model is successfully predicting glucose concentrations from noninvasive spectra for a larger number of individuals, FIGS. 12 and 13. Further, the in-vitro model is performing at a level substantially equivalent to the in-vivo based models. This demonstrates that models generated with the in-vitro spectra of the tissue phantom matrix are successfully used to accurately and precisely predict glucose concentrations from noninvasive spectra of the human arm.

CONCLUSION

A family of samples with scattering properties closely matching skin tissue is generated. Additional sample components that represent all of the major near-infrared absorbers present in skin are independently added to the matrix. The experimental design preferably uses the additional interferences to break all correlations of glucose concentration with the concentrations of all other sample constituents and with time. An f-test using references collected with the spectra demonstrates that subsequent multivariate analyses are not modeling environmental effects on the spectrometer. Multivariate analyses demonstrate successful diffuse reflectance measurements of glucose in each of the three spectral regions (combination band, $1^{st}$ overtone, and second overtone) where glucose absorbance in the near-infrared is demonstrated. The results are supported with interpretations of spectral loadings and noise levels.

Models generated with the in-vitro spectra of the tissue phantom matrix are successfully used to accurately and precisely predict glucose concentrations from noninvasive spectra of the human arm. Further, the in-vivo model, is strongly correlated with the in-vivo model. This is extremely strong evidence that the in-vivo model is determining the glucose concentration rather than some ancillary sample constituent, human physiological effect, or environmental condition.

Although the invention has been described herein with reference to certain preferred embodiments, one skilled in the art will readily appreciate that other applications are optionally substituted for those set forth herein without departing from the spirit and scope of the present invention. Accordingly, the invention should only be limited by the claims included below.

The invention claimed is:

1. A computer implemented method for noninvasively estimating an analyte concentration with an in-vivo instrument system, comprising the steps of:
   providing a first model;
   removing at least one interference from said first model to form a second model;
   standardizing said in-vivo instrument system to said second model to generate a third model;
   providing an in-vivo test set, comprising:
      at least one in-vivo test signal; and
      a reference analyte concentration corresponding with said in-vivo test signal;
   applying said third model to said in-vivo test signal to generate a test value;
   applying a correction to said third model using said test value and said reference analyte concentration to yield a corrected third model;
   providing an in-vivo measurement signal; and
   estimating and providing for use said analyte concentration using said corrected third model and said in-vivo measurement signal.

2. The method of claim 1, wherein said first model comprises coefficients generated at least in part with an in-vitro data set.

3. The method of claim 2, wherein said third model comprises a third set of coefficients.

4. The method of claim 3, wherein said analyte concentration comprises a glucose concentration.

5. The method of claim 4, wherein said first model comprises coefficients derived from data comprised of at least twenty percent in-vitro data.

6. The method of claim 5, wherein said first model comprises coefficients derived from data comprised of at least eighty percent in-vitro data.

7. The method of claim 4, wherein said step of applying a correction comprises the step of at least one of:
   applying an offset; and
   applying a scaling factor.

8. The method of claim 7, further comprising:
   repeating said steps of providing an in-vivo test set, applying said second model to said in-vivo test set, applying a correction, and applying an offset.

9. The method of claim 3, wherein said step of removing comprises projecting said coefficients onto a null space of said interference.

10. The method of claim 9, wherein said interference comprises at least one of:
   a protein signal;
   a fat signal;
   a water signal;
   a salt signal;
   a thermal noise;
   a specific tissue sample spectrum;
   an individual;

a class of subjects; and
a cluster of data.

11. The method of claim 3, wherein said step of standardizing comprises the step of at least one of:
smoothing;
interpolating;
scaling;
filtering;
performing an offset correction;
performing a bias correction;
normalizing;
performing direct standardization
performing piece-wise direct standardization;
performing a standard normal variate transformation;
performing multiplicative scatter correction;
performing orthogonal signal correction;
re-sampling; and
correcting wavelength.

12. The method of claim 11, wherein said step of standardizing comprises at least three of:
smoothing;
interpolating;
scaling;
filtering;
performing offset correction
performing bias correction;
normalizing;
performing direct standardization
performing piece-wise direct standardization;
performing standard normal variate transformation;
performing multiplicative scatter correction;
performing orthogonal signal correction;
re-sampling; and
correcting wavelength.

13. The method of claim 3, wherein said in-vivo test signal comprises a spectrum.

14. The method of claim 3, wherein said second model comprises coefficients generated on a first instrument and said third model comprises coefficients generated on a second instrument.

15. The method of claim 14, wherein said first instrument comprises a research grade spectrometer.

16. The method of claim 14, wherein said second instrument comprises a production grade analyzer.

17. The method of claim 3, wherein said in-vivo measurement signal comprises a spectrum.

18. The method of claim 3, further comprising the step of:
housing at least one of said first model, said second model, and said third model in an analyzer.

19. The method of claim 18, further comprising the step of:
providing an analyzer that comprises:
a base module;
a communication bundle with a first end and a second end, wherein said first end is connected to said base module;
a sample module, wherein said second end of said communication bundle is connected to said sample module; and
a processor.

20. A computer implemented method for noninvasive estimation of a sample constituent property, comprising the steps of:
providing a noninvasive signal;
providing a first model, wherein said first model comprises coefficients that are generated at least in part with an in-vitro data set, wherein said in-vitro data set comprises a spectrum of a tissue phantom having at least one optical parameter representative of said noninvasive signal in terms of photonic scattering and/or absorbance;
standardizing an in-vivo instrument system to said first model, wherein a second model is generated; and
estimating and providing for use said sample property by applying said second model to said noninvasive signal.

21. The method of claim 20, wherein said step of standardizing comprises the step of at least one of:
smoothing;
interpolating;
scaling;
filtering;
performing offset correction
performing bias correction;
normalizing;
performing direct standardization
performing piece-wise direct standardization;
performing standard normal variate transformation;
performing multiplicative scatter correction;
performing orthogonal signal correction;
re-sampling; and
correcting wavelength.

22. The method of claim 21, wherein said step of standardizing comprises the step of at least three of:
smoothing;
interpolating;
scaling;
filtering;
performing offset correction
performing bias correction;
normalizing;
performing direct standardization
performing piece-wise direct standardization;
performing standard normal variate transformation;
performing multiplicative scatter correction;
performing orthogonal signal correction;
re-sampling; and
correcting wavelength.

23. The method of claim 20, wherein said sample property comprises a glucose concentration.

24. The method of claim 20, wherein said data set comprises data that are collected with a first analyzer, and said noninvasive signal comprises a signal that is collected with a second analyzer.

25. The method of claim 24, wherein said first analyzer comprises a research grade instrument.

26. The method of claim 24, wherein said second analyzer comprises a production analyzer.

27. The method of claim 24, wherein said second analyzer comprises a base module in a first container and a sample module in a second container.

28. The method of claim 20, wherein said first model is generated with at least eighty percent in-vitro data.

29. An apparatus for noninvasive estimation of a sample constituent property from a noninvasive spectrum, comprising:
an analyzer comprising a base module, a sample module, and a model residing in said analyzer;
wherein said model comprises coefficients generated by standardizing an in-vivo system to an in-vitro data set,
wherein said in-vitro data set comprises a spectrum of a tissue phantom having at least one optical parameter representative of said noninvasive spectrum in terms of photonic scattering and/or absorbance; and
wherein said model is applied to said noninvasive spectrum for estimation of said sample constituent property.

30. The apparatus of claim 29, wherein said base module resides in a first container and said sample module resides in a second container.

31. A computer implemented method for noninvasive estimation of a sample constituent property, comprising the steps of:
providing a first model, wherein said first model comprises coefficients that are generated at least in part with an in-vitro data set;
standardizing an in-vivo instrument system to said first model to generate a second model, wherein said second model comprises a second set of coefficients;
providing an in-vivo test set, comprising:
at least one in-vivo test signal; and
a reference sample concentration that is correlated with said in-vivo test signal;
applying said second model to said in-vivo test set to generate a test value;
providing an in-vivo measurement signal; and
estimating and providing for use said sample constituent property using said second model and said in-vivo measurement signal, wherein said step of estimating comprises multiplication of said in-vivo measurement signal by both a regression vector and a scaling factor resulting in a product that is adjusted with an offset.

32. The method of claim 31, wherein said test signal comprises a spectrum.

33. The method of claim 31, wherein said sample constituent property comprises a glucose concentration.

34. The method of claim 33, further comprising the step of:
repeating said steps of providing an in-vivo test set, applying said second model to said in-vivo test set, applying a correction, and applying an offset.

35. The method of claim 33, wherein said estimated glucose concentration is determined according to:

$$\hat{y} = xaW + b$$

where a is said scaling factor, b is said offset, x is said in-vivo test measurement signal, W is said regression vector of said second model, and $\hat{y}$ is said estimated glucose concentration.

36. The method of claim 31, wherein said first model comprises coefficients generated using a first instrument and said test signal comprises signals generated on a second instrument.

37. The method of claim 36, wherein said first instrument comprises a research grade spectrometer.

38. The method of claim 36, wherein said second instrument comprises a production grade spectrometer.

39. The method of claim 31, wherein said first model comprises coefficients generated with a research grade spectrometer.

40. The method of claim 31, wherein said in-vivo instrument system comprises a production grade analyzer.

41. The method of claim 31, wherein said first model is generated with at least twenty percent in-vitro data.

42. The method of claim 41, wherein said first model is generated with at least eighty percent in-vitro data.

43. The method of claim 31, wherein said step of standardizing comprises the step of at least one of:
smoothing;
interpolating;
scaling;
filtering;
performing offset correction
performing bias correction;
normalizing;
performing direct standardization
performing piece-wise direct standardization;
performing standard normal variate transformation;
performing multiplicative scatter correction;
performing orthogonal signal correction;
re-sampling; and
correcting wavelength.

44. A computer implemented method for noninvasively estimating an analyte concentration, comprising the steps of:
providing a first calibration model;
removing at least one interference from said first model to form a second model, wherein said first model comprises coefficients derived from data comprised of at least twenty percent in-vitro data, wherein said step of removing comprises projecting said coefficients onto a null space of said interference;
providing an in-vivo signal; and
estimating and providing for use said analyte concentration using said second model and said in-vivo signal.

45. The method of claim 44, wherein said first model comprises coefficients derived from data comprised of at least eighty percent in-vitro data.

46. The method of claim 44, wherein said analyte concentration comprises a glucose concentration.

47. The method of claim 44, wherein said step of removing comprises subtraction.

48. The method of claim 44, wherein said interference comprises at least one of:
protein;
fat;
a specific tissue sample;
an individual;
a class of subjects; and
a cluster of data.

49. An apparatus for noninvasive estimation of a sample constituent property from a noninvasive spectrum, comprising:
an analyzer, comprising:
a base module;
a sample module; and
a model residing in said analyzer;
wherein said model comprises coefficients generated by standardizing an in-vivo system to a model of coefficients derived at least in part from an in-vitro data set;
wherein said in-vitro signal comprises a spectrum of a tissue phantom having at least one optical parameter representative of said noninvasive spectrum in terms of photonic scattering and/or absorbance; and
wherein said model is applied to said noninvasive spectrum to generate said sample constituent property.

50. The apparatus of claim 49, wherein said model further comprises a correction to said model.

51. The apparatus of claim 50, wherein said correction comprises at least one of:
an offset; and
a scaling factor.

52. The apparatus of claim 49, wherein said base module resides in a first container and said sample module resides in a second container.

53. The apparatus of claim 52, further comprising:
a communication bundle;
wherein said communication bundle interfaces said base module to said sample module.

54. A computer implemented method for noninvasively estimating a blood/tissue glucose concentration, comprising the steps of:
- providing a noninvasive near-infrared signal;
- providing a calibration model;
- supplementing said calibration model with an in-vitro signal, wherein said in-vitro signal comprises a spectrum of a tissue phantom having at least one optical parameter representative of said noninvasive near-infrared signal in terms of photonic scattering and/or absorbance; and
- estimating and providing for use said blood glucose concentration using said model and said noninvasive signal.

55. The method of claim 54, further comprising the steps of:
- providing an in-vivo test set, comprising:
  - at least one in-vivo test signal; and
  - a reference glucose concentration that is correlated with said in-vivo test signal;
- applying said model to said in-vivo test signal to generate a test value; and
- determining a correction to said model using said test value and said reference glucose concentration.

56. The method of claim 55, further comprising the step of:
- repeating said steps of providing an in-vivo test set; applying said model to said in-vivo test signal to generate a test value; and determining a correction to said model using said test value and said reference glucose concentration.

57. The method of claim 56, further comprising the step of:
- removing at least one interference from said model.

58. A computer implemented method for noninvasive estimation of a sample constituent property from an in-vivo instrument system, comprising the steps of:
- providing a noninvasive signal;
- providing a model, comprising coefficients generated at least in part with an in-vitro data set, wherein said in-vitro data set comprises a spectrum of a tissue phantom having at least one optical parameter representative of said noninvasive spectrum in terms of photonic scattering and/or absorbance;
- standardizing said model to said in-vivo instrument system; and
- estimating and providing for use said sample property by applying said model to said noninvasive signal.

59. The method of claim 58, wherein said step of standardizing comprises the step of at least one of:
- smoothing;
- interpolating;
- scaling;
- filtering;
- performing offset correction
- performing bias correction;
- normalizing;
- performing direct standardization
- performing piece-wise direct standardization;
- performing standard normal variate transformation;
- performing multiplicative scatter correction;
- performing orthogonal signal correction;
- re-sampling; and
- correcting wavelength.

60. The method of claim 59, wherein said step of standardizing comprises the step of at least three of:
- smoothing;
- interpolating;
- scaling;
- filtering;
- performing offset correction
- performing bias correction;
- normalizing;
- performing direct standardization
- performing piece-wise direct standardization;
- performing standard normal variate transformation;
- performing multiplicative scatter correction;
- performing orthogonal signal correction;
- re-sampling; and
- correcting wavelength.

61. The method of claim 58, wherein said sample property comprises a glucose concentration.

62. The method of claim 58, wherein said data set comprises data that are collected with a first analyzer and said noninvasive signal comprises a signal that is collected with a second analyzer.

63. The method of claim 62, wherein said first analyzer comprises a research grade instrument.

64. The method of claim 62, wherein said second analyzer comprises a production analyzer.

65. The method of claim 62, wherein said second analyzer comprises a base module residing a first container and a sample module residing in a second container.

66. The method of claim 58, wherein said model is generated with at least eighty percent in-vitro data.

* * * * *